(12) United States Patent
D'Acosta et al.

(10) Patent No.: US 10,526,554 B2
(45) Date of Patent: *Jan. 7, 2020

(54) TREATING C8-C10 AROMATIC FEED STREAMS TO PREPARE AND RECOVER TRIMETHYLATED BENZENES

(71) Applicant: Swift Fuels, LLC, West Lafayette, IN (US)

(72) Inventors: Chris D'Acosta, West Lafayette, IN (US); Jeffery Miller, Naperville, IL (US); Robert Hoch, Hensonville, NY (US)

(73) Assignee: SWIFT FUELS, LLC, West Lafayette, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/864,777

(22) Filed: Jan. 8, 2018

(65) Prior Publication Data

US 2018/0201848 A1 Jul. 19, 2018

Related U.S. Application Data

(60) Provisional application No. 62/443,292, filed on Jan. 6, 2017.

(51) Int. Cl.
*C10G 69/00* (2006.01)
*C10G 69/12* (2006.01)

(52) U.S. Cl.
CPC ..... *C10G 69/123* (2013.01); *C10G 2300/1096* (2013.01); *C10G 2300/4081* (2013.01); *C10G 2400/30* (2013.01)

(58) Field of Classification Search
CPC ......... C10G 69/123; C07C 9/00; C07C 37/74; C07C 6/12; C07C 6/123; C07C 6/06; B01J 20/183; B01J 27/13; B01J 29/18
USPC ........................................ 585/253
See application file for complete search history.

(56) References Cited

U.S. PATENT DOCUMENTS

| | | | |
|---|---|---|---|
| 2,593,561 A | 4/1952 | Herbst et al. | |
| 3,253,049 A | 5/1966 | Allen et al. | |
| 3,260,764 A | 7/1966 | Kovach et al. | |
| 3,412,521 A | 11/1968 | Bauman | |
| 3,677,973 A | 7/1972 | Mitsche et al. | |
| 4,172,813 A | 10/1979 | Feinstein et al. | |
| 5,004,864 A | 4/1991 | Yin | |
| 5,156,901 A | 10/1992 | Tanaka | |
| 5,197,659 A | 3/1993 | Vassiliou | |
| 5,285,957 A | 2/1994 | Halsell | |
| 5,417,342 A | 5/1995 | Hutchison | |
| 5,698,757 A | 12/1997 | Wu et al. | |
| 5,702,053 A | 12/1997 | Kozakai | |
| 5,799,861 A | 9/1998 | Bonner et al. | |
| 6,079,617 A | 6/2000 | Kim | |
| 6,136,155 A | 10/2000 | Berg | |
| 6,138,903 A | 10/2000 | Baker | |
| 6,189,330 B1 | 2/2001 | Retallick | |
| 6,325,281 B1 | 12/2001 | Grogan | |
| 6,536,654 B2 | 3/2003 | Reynolds | |
| 7,094,192 B2 | 8/2006 | Schoenberger | |
| 7,157,397 B2 | 1/2007 | Dalloro et al. | |
| 7,229,677 B2 | 6/2007 | Miller | |
| 8,049,048 B2 | 11/2011 | Rusek et al. | |
| 9,890,095 B2 * | 2/2018 | D'Acosta | C07C 4/18 |
| 2002/0000297 A1 | 1/2002 | Kitano et al. | |
| 2003/0226882 A1 | 12/2003 | Porchia et al. | |
| 2005/0214512 A1 | 9/2005 | Fascio | |
| 2005/0224501 A1 | 10/2005 | Folkert et al. | |
| 2007/0000983 A1 | 1/2007 | Spurrell | |
| 2007/0051782 A1 | 3/2007 | Lantz | |
| 2008/0041860 A1 | 2/2008 | Wiedmeyer | |
| 2008/0086982 A1 | 4/2008 | Parenteau | |
| 2008/0087716 A1 | 4/2008 | Sadlier | |
| 2008/0276643 A1 | 11/2008 | Heroux et al. | |
| 2012/0067774 A1 | 3/2012 | Frey et al. | |
| 2014/0316173 A1 | 10/2014 | Watermeyer De Wet et al. | |
| 2014/0316174 A1 * | 10/2014 | D'Acosta | C07C 2/66 585/24 |

FOREIGN PATENT DOCUMENTS

| | | |
|---|---|---|
| CN | 102 746 092 A | 10/2012 |
| JP | 2002-226406 A | 8/2002 |
| KR | 10-2012-0118272 A | 10/2012 |
| WO | WO 2008/073118 A1 | 6/2008 |

OTHER PUBLICATIONS

Al-Khattaf, Sulaiman et al. "1,2,4-Trimethylbenzene Transformation Reaction Compared with its Transalkylation Reaction with Toulene over USY-Zeolite Catalyst," Chemical Eng. Dept., King Fahd Univ of Petroleum & Minerals,Dhahran, Saudi Arabia, Feb. 2007, pp. 1-29.

C. J. Egan, "Calculated Equilibria of the Methylbenzenes and Benzene from 298 Degrees to 1000 Degrees K," Journal of Chemical and Engineering Data, vol. 5, No. 3, Jul. 1960, pp. 298-299.

English Abstract of JP 2002-226406A to Toray IND., Inc., Aug. 14, 2002.

English Abstract of KR 1020120118272A to S-Oil Corporation, et al., Oct. 26, 2012.

Heinz Heinemann, Founding Editor, "Catalytic Naphtha Reforming" 2nd Edition, edited by GJ. Antos and A. M. Aitani, NY, Marcel Dekker, Inc. 2004, pp. 1-617.

International Search Report and Witten Opinion issued in PCT/US2014/034681, dated Sep. 25 2014, 11 pgs.

(Continued)

*Primary Examiner* — Sharon Pregler
(74) *Attorney, Agent, or Firm* — Woodard, Emhardt, Henry, Reeves & Wagner, LLP

(57) ABSTRACT

Methods and alternatives for the efficient and cost-effective production of high-octane fuel blends from C9 aromatic feeds including methyl benzenes and C2 and/or higher alkyl benzenes. The fuel blend can serve as a high-octane unleaded fuel or fuel blending component for a wide range of applications, particularly aviation gasoline and other high-performance transportation fuels.

26 Claims, 36 Drawing Sheets

(56) References Cited

OTHER PUBLICATIONS

M. R. Rahimpour, et al., "Progress in catalytic naphtha reforming process: A review," Applied Energy, vol. 109, 2013, pp. 79-93.
S.A. All et al., "Conversion of heavy reformats into xylenes over morderilte-based catalysts," Chemical Eng. Research and Design, vol. 89, 2011, pp. 2125-2135.
English Abstract of CN 102 746 092A.
International Application PCT/US2018/012801 International Search Report and Written Opinion dated Mar. 6, 2018.

* cited by examiner

Figure One
Block Flow Diagram for
Two Lights Column Design
including Lights Recycle

| STREAM NUMBER | | 2 | 3 | 4 | 5 | 19 | 30 | 38 |
|---|---|---|---|---|---|---|---|---|
| TEMPERATURE | DEG F | 82 | 111 | 339 | 761 | 392 | 350 | 148 |
| PRESSURE | PSIA | 405 | 405 | 405 | 400 | 330 | 330 | 405 |
| COMPONENTS | | | | | | | | |
| HYDROGEN | LB/HR | 0 | 6,281 | 6,281 | 6,281 | 5,806 | 5,806 | 6,281 |
| METHANE | LB/HR | 0 | 0 | 0 | 0 | 0 | 0 | 0 |
| WATER | LB/HR | 0 | 0 | 0 | 0 | 0 | 0 | 0 |
| ETHANE | LB/HR | 0 | 1,037 | 1,037 | 1,037 | 7,406 | 7,406 | 1,037 |
| PROPANE | LB/HR | 0 | 0 | 0 | 0 | 761 | 761 | 0 |
| BUTANE | LB/HR | 0 | 0 | 0 | 0 | 341 | 341 | 0 |
| TOLUENE | LB/HR | 0 | 0 | 0 | 0 | 4,509 | 4,509 | 0 |
| BENZENE | LB/HR | 0 | 0 | 0 | 0 | 0 | 0 | 0 |
| O_XYLENE | LB/HR | 0 | 0 | 0 | 0 | 5,474 | 5,474 | 0 |
| 124TRIMETHYLBENZENE | LB/HR | 23,827 | 23,827 | 23,827 | 23,827 | 31,467 | 31,467 | 0 |
| 1ETHYL2METHYLBENZENE | LB/HR | 10,808 | 10,808 | 10,808 | 10,808 | 0 | 0 | 0 |
| 1ETHYL4METHYLBENZENE | LB/HR | 5,328 | 5,328 | 5,328 | 5,328 | 0 | 0 | 0 |
| 123TRIMETHYLBENZENE | LB/HR | 4,544 | 4,544 | 4,544 | 4,544 | 1,666 | 1,666 | 0 |
| 135TRIMETHYLBENZENE | LB/HR | 3,445 | 3,445 | 3,445 | 3,445 | 14,435 | 14,435 | 0 |
| M_XYLENE | LB/HR | 1,707 | 1,707 | 1,707 | 1,707 | 14,641 | 14,641 | 0 |
| 13DIETHYLBENZENE | LB/HR | 3,392 | 3,392 | 3,392 | 3,392 | 0 | 0 | 0 |
| 2ETHYL13DIMETHYLBENZENE | LB/HR | 1,559 | 1,559 | 1,559 | 1,559 | 0 | 0 | 0 |
| 1METHYL3PROPYLBENZENE | LB/HR | 1,088 | 1,088 | 1,088 | 1,088 | 0 | 0 | 0 |
| 1ETHYL23DIMETHYLBENZENE | LB/HR | 857 | 857 | 857 | 857 | 0 | 0 | 0 |
| 1245TETRAMETHYLBENZENE | LB/HR | 1,230 | 1,230 | 1,230 | 1,230 | 19,532 | 19,532 | 0 |
| 1ETHYL24DIMETHYLBENZENE | LB/HR | 705 | 705 | 705 | 705 | 0 | 0 | 0 |
| PROPYLBENZENE | LB/HR | 571 | 571 | 571 | 571 | 0 | 0 | 0 |
| M_CYMENE | LB/HR | 486 | 486 | 486 | 486 | 0 | 0 | 0 |
| SEC_BUTYLBENZENE | LB/HR | 632 | 632 | 632 | 632 | 0 | 0 | 0 |
| 1234TETRAMETHYLBENZENE | LB/HR | 334 | 334 | 334 | 334 | 445 | 445 | 0 |
| 1ETHYL2DIMETHYLBENZENE | LB/HR | 276 | 276 | 276 | 276 | 0 | 0 | 0 |
| P_XYLENE | LB/HR | 176 | 176 | 176 | 176 | 5,590 | 5,590 | 0 |
| NAPTHALENE | LB/HR | 247 | 247 | 247 | 247 | 0 | 0 | 0 |
| BUTYLBENZENE | LB/HR | 156 | 156 | 156 | 156 | 0 | 0 | 0 |
| 12DIETHYLBENZENE | LB/HR | 113 | 113 | 113 | 113 | 0 | 0 | 0 |
| 2METHYL1PROPYLBENZENE | LB/HR | 102 | 102 | 102 | 102 | 0 | 0 | 0 |
| 1235TETRAMETHYLBENZENE | LB/HR | 0 | 0 | 0 | 0 | 5,767 | 5,767 | 0 |
| PENTAMETHYLBENZENE | LB/HR | 0 | 0 | 0 | 0 | 1,986 | 1,986 | 0 |
| BICYCLOHEXYL | LB/HR | 2,496 | 2,496 | 2,496 | 2,496 | 0 | 0 | 0 |
| | | | | | | | | |
| TOTAL | LB/HR | 64,080 | 71,398 | 71,398 | 71,398 | 119,825 | 119,825 | 7,318 |
| ENTHALPY | BTU/LB | -222 | -195 | 5 | 431 | 58 | -63 | 42 |
| DENSITY | LB/CUFT | 54.36 | 1.46 | 1.02 | 0.59 | 1.07 | 1.33 | 0.14 |
| VOLUMETRIC_FLOW | GPM | 147 | 6,089 | 8,757 | 14,983 | 13,955 | 11,253 | 6,323 |

FIG. 5B

| STREAM NUMBER | | 1 | 2 |
|---|---|---|---|
| TEMPERATURE | DEG F | 77 | 82 |
| PRESSURE | PSIA | 15 | 405 |
| COMPONENTS | | | |
| | | | |
| HYDROGEN | LB/HR | 0 | 0 |
| METHANE | LB/HR | 0 | 0 |
| WATER | LB/HR | 0 | 0 |
| ETHANE | LB/HR | 0 | 0 |
| PROPANE | LB/HR | 0 | 0 |
| BUTANE | LB/HR | 0 | 0 |
| TOLUENE | LB/HR | 0 | 0 |
| BENZENE | LB/HR | 0 | 0 |
| O_XYLENE | LB/HR | 0 | 0 |
| 124TRIMETHYLBENZENE | LB/HR | 23,827 | 23,827 |
| 1ETHYL2METHYLBENZENE | LB/HR | 10,808 | 10,808 |
| 1ETHYL4METHYLBENZENE | LB/HR | 5,328 | 5,328 |
| 123TRIMETHYLBENZENE | LB/HR | 4,544 | 4,544 |
| 135TRIMETHYLBENZENE | LB/HR | 3,445 | 3,445 |
| M_XYLENE | LB/HR | 1,707 | 1,707 |
| 13DIETHYLBENZENE | LB/HR | 3,392 | 3,392 |
| 2ETHYL13DIMETHYLBENZENE | LB/HR | 1,559 | 1,559 |
| 1METHYL3PROPYLBENZENE | LB/HR | 1,088 | 1,088 |
| 1ETHYL23DIMETHYLBENZENE | LB/HR | 857 | 857 |
| 1245TETRAMETHYLBENZENE | LB/HR | 1,230 | 1,230 |
| 1ETHYL24DIMETHYLBENZENE | LB/HR | 705 | 705 |
| PROPYLBENZENE | LB/HR | 571 | 571 |
| M_CYMENE | LB/HR | 486 | 486 |
| SEC_BUTYLBENZENE | LB/HR | 632 | 632 |
| 1234TETRAMETHYLBENZENE | LB/HR | 334 | 334 |
| 4ETHYL12DIMETHYLBENZENE | LB/HR | 276 | 276 |
| P_XYLENE | LB/HR | 176 | 176 |
| NAPTHALENE | LB/HR | 247 | 247 |
| BUTYLBENZENE | LB/HR | 156 | 156 |
| 12DIETHYLBENZENE | LB/HR | 113 | 113 |
| 2METHYL1PROPYLBENZENE | LB/HR | 102 | 102 |
| 1235TETRAMETHYLBENZENE | LB/HR | 0 | 0 |
| PENTAMETHYLBENZENE | LB/HR | 0 | 0 |
| BICYCLOHEXYL | LB/HR | 2,496 | 2,496 |
| | | | |
| TOTAL | LB/HR | 64,080 | 64,080 |
| ENTHALPY | BTU/LB | -224 | -222 |
| DENSITY | LB/CUFT | 54.51 | 54.36 |
| VOLUMETRIC_FLOW | GPM | 147 | 147 |

FIG. 6B

| STREAM NUMBER | | 5 | 6 | 7 | 8 | 9 | 10 | 11 |
|---|---|---|---|---|---|---|---|---|
| TEMPERATURE | DEG F | 761 | 932 | 761 | 932 | 761 | 932 | 392 |
| PRESSURE | PSIA | 400 | 390 | 380 | 370 | 360 | 350 | 340 |
| COMPONENTS | MW | | | | | | | |
| HYDROGEN | | 6,381 | 6,123 | 6,123 | 5,910 | 5,910 | 5,806 | 5,806 |
| METHANE | | 0 | 0 | 0 | 0 | 0 | 0 | 0 |
| WATER | | 0 | 0 | 0 | 0 | 0 | 0 | 0 |
| ETHANE | | 1,037 | 3,160 | 3,160 | 6,005 | 6,005 | 7,406 | 7,406 |
| PROPANE | | 0 | 254 | 254 | 503 | 503 | 761 | 761 |
| BUTANE | | 0 | 114 | 114 | 266 | 266 | 341 | 341 |
| TOLUENE | | 0 | 4,507 | 4,507 | 10,547 | 10,547 | 13,522 | 13,522 |
| BENZENE | | 0 | 957 | 957 | 2,239 | 2,239 | 2,870 | 2,870 |
| O_XYLENE | | 0 | 299 | 299 | 699 | 699 | 896 | 896 |
| 124TRIMETHYLBENZENE | | 23,827 | 23,827 | 23,827 | 23,827 | 23,827 | 23,827 | 23,827 |
| 1ETHYL3METHYLBENZENE | | 10,808 | 7,205 | 7,205 | 2,378 | 2,378 | 0 | 0 |
| 1ETHYL4METHYLBENZENE | | 5,328 | 3,552 | 3,552 | 1,172 | 1,172 | 0 | 0 |
| 123TRIMETHYLBENZENE | | 4,544 | 4,544 | 4,544 | 4,544 | 4,544 | 4,544 | 4,544 |
| 135TRIMETHYLBENZENE | | 3,445 | 3,445 | 3,445 | 3,445 | 3,445 | 3,445 | 3,445 |
| M_XYLENE | | 1,702 | 2,304 | 2,304 | 3,104 | 3,104 | 3,498 | 3,498 |
| 13DIETHYLBENZENE | | 3,392 | 2,262 | 2,262 | 746 | 746 | 0 | 0 |
| 2ETHYL13DIMETHYLBENZENE | | 1,549 | 1,040 | 1,040 | 343 | 343 | 0 | 0 |
| 1METHYL3PROPYLBENZENE | | 1,088 | 725 | 725 | 239 | 239 | 0 | 0 |
| 1ETHYL23DIMETHYLBENZENE | | 857 | 572 | 572 | 189 | 189 | 0 | 0 |
| 1245TETRAMETHYLBENZENE | | 1,230 | 1,230 | 1,230 | 1,230 | 1,230 | 1,230 | 1,230 |
| 1ETHYL24DIMETHYLBENZENE | | 705 | 470 | 470 | 155 | 155 | 0 | 0 |
| PROPYLBENZENE | | 571 | 381 | 381 | 126 | 126 | 0 | 0 |
| M_CYMENE | | 486 | 324 | 324 | 107 | 107 | 0 | 0 |
| SEC_BUTYLBENZENE | | 632 | 421 | 421 | 139 | 139 | 0 | 0 |
| 1234TETRAMETHYLBENZENE | | 334 | 334 | 334 | 334 | 334 | 334 | 334 |
| 4ETHYL12DIMETHYLBENZENE | | 276 | 184 | 184 | 61 | 61 | 0 | 0 |
| P_XYLENE | | 176 | 176 | 176 | 176 | 176 | 176 | 176 |
| NAPTHALENE | | 247 | 247 | 247 | 247 | 247 | 247 | 247 |
| BUTYLBENZENE | | 156 | 104 | 104 | 34 | 34 | 0 | 0 |
| 12DIETHYLBENZENE | | 113 | 75 | 75 | 25 | 25 | 0 | 0 |
| 2METHYL1PROPYLBENZENE | | 102 | 68 | 68 | 23 | 23 | 0 | 0 |
| 1235TETRAMETHYLBENZENE | | 0 | 0 | 0 | 0 | 0 | 0 | 0 |
| PENTAMETHYLBENZENE | | 0 | 0 | 0 | 0 | 0 | 0 | 0 |
| BICYCLOHEXYL | | 2,496 | 2,496 | 2,496 | 2,496 | 2,496 | 2,496 | 2,496 |
| TOTAL | LB/HR | 71,398 | 71,398 | 71,398 | 71,398 | 71,398 | 71,398 | 71,398 |
| ENTHALPY | BTU/LB | 434 | 560 | 412 | 534 | 386 | 520 | 93 |
| DENSITY | LB/CUFT | 0.59 | 0.51 | 0.56 | 0.48 | 0.53 | 0.46 | 0.73 |
| VOLUMETRIC_FLOW | GPM | 14,983 | 17,518 | 15,770 | 18,463 | 16,645 | 19,517 | 12,001 |

FIG. 7B

| STREAM NUMBER | | 11 | 12 | 19 | 41 |
|---|---|---|---|---|---|
| TEMPERATURE | DEG F | 392 | 396 | 392 | 392 |
| PRESSURE | PSIA | 340 | 340 | 330 | 340 |
| COMPONENTS | MW | | | | |
| | | | | | |
| HYDROGEN | | 5,806 | 5,806 | 5,806 | 0 |
| METHANE | | 0 | 0 | 0 | 0 |
| WATER | | 0 | 0 | 0 | 0 |
| ETHANE | | 7,406 | 7,406 | 7,406 | 0 |
| PROPANE | | 761 | 761 | 761 | 0 |
| BUTANE | | 341 | 341 | 341 | 0 |
| TOLUENE | | 13,522 | 13,522 | 4,509 | 0 |
| BENZENE | | 2,870 | 2,870 | 0 | 0 |
| O_XYLENE | | 896 | 896 | 5,474 | 0 |
| 124TRIMETHYLBENZENE | | 23,827 | 43,691 | 31,467 | 21,865 |
| 1ETHYL2METHYLBENZENE | | 0 | 0 | 0 | 0 |
| 1ETHYL4METHYLBENZENE | | 0 | 0 | 0 | 0 |
| 123TRIMETHYLBENZENE | | 4,344 | 6,040 | 1,666 | 1,497 |
| 135TRIMETHYLBENZENE | | 3,445 | 3,561 | 14,435 | 115 |
| M_XYLENE | | 3,498 | 3,498 | 14,641 | 0 |
| 13DIETHYLBENZENE | | 0 | 0 | 0 | 0 |
| 2ETHYL13DIMETHYLBENZENE | | 0 | 0 | 0 | 0 |
| 1METHYL3PROPYLBENZENE | | 0 | 0 | 0 | 0 |
| 1ETHYL23DIMETHYLBENZENE | | 0 | 0 | 0 | 0 |
| 1245TETRAMETHYLBENZENE | | 1,230 | 18,803 | 19,532 | 17,573 |
| 1ETHYL24DIMETHYLBENZENE | | 0 | 0 | 0 | 0 |
| PROPYLBENZENE | | 0 | 0 | 0 | 0 |
| M_CYMENE | | 0 | 0 | 0 | 0 |
| SEC_BUTYLBENZENE | | 0 | 0 | 0 | 0 |
| 1234TETRAMETHYLBENZENE | | 334 | 734 | 443 | 400 |
| 4ETHYL12DIMETHYLBENZENE | | 0 | 0 | 0 | 0 |
| P_XYLENE | | 176 | 176 | 5,590 | 0 |
| NAPTHALENE | | 247 | 247 | 0 | 0 |
| BUTYLBENZENE | | 0 | 0 | 0 | 0 |
| 12DIETHYLBENZENE | | 0 | 0 | 0 | 0 |
| 2METHYL1PROPYLBENZENE | | 0 | 0 | 0 | 0 |
| 1235TETRAMETHYLBENZENE | | 0 | 5,189 | 5,767 | 5,189 |
| PENTAMETHYLBENZENE | | 0 | 1,787 | 1,986 | 1,787 |
| BICYCLOHEXYL | | 2,496 | 2,496 | 0 | 0 |
| | | | | | |
| TOTAL | LB/HR | 71,398 | 119,825 | 119,825 | 48,427 |
| ENTHALPY | BTU/LB | 65 | -6 | 56 | -111 |
| DENSITY | LB/CUFT | 0.74 | 1.24 | 1.07 | 45.27 |
| VOLUMETRIC_FLOW | GPM | 12,001 | 12,063 | 13,955 | 133 |

FIG. 8B

| STREAM NUMBER | | 30 | 45 | 46 | 47 | 48 | 51 | 70 | 74 |
|---|---|---|---|---|---|---|---|---|---|
| TEMPERATURE | DEG F | 350 | 200 | 200 | 150 | 101 | 159 | 100 | 200 |
| PRESSURE | PSIA | 330 | 335 | 335 | 330 | 320 | 321 | 330 | 340 |
| COMPONENTS | MW | | | | | | | | |
| HYDROGEN | | 5,806 | 5,803 | 3 | 3 | 5,803 | 3 | 3 | 5,806 |
| METHANE | | 0 | 0 | 0 | 0 | 0 | 0 | 0 | 0 |
| WATER | | 0 | 0 | 0 | 0 | 0 | 0 | 0 | 0 |
| ETHANE | | 7,406 | 7,067 | 339 | 339 | 6,914 | 492 | 339 | 7,406 |
| PROPANE | | 761 | 654 | 107 | 107 | 574 | 182 | 107 | 761 |
| BUTANE | | 341 | 230 | 112 | 112 | 71 | 279 | 112 | 341 |
| TOLUENE | | 4,509 | 389 | 4,120 | 4,120 | 48 | 4,461 | 4,120 | 4,509 |
| BENZENE | | 0 | 0 | 0 | 0 | 0 | 0 | 0 | 0 |
| O_XYLENE | | 5,474 | 168 | 5,306 | 5,306 | 15 | 5,459 | 5,306 | 5,474 |
| 124TRIMETHYLBENZENE | | 31,467 | 425 | 31,043 | 31,042 | 31 | 31,436 | 31,042 | 31,467 |
| 1ETHYL2METHYLBENZENE | | 0 | 0 | 0 | 0 | 0 | 0 | 0 | 0 |
| 1ETHYL4METHYLBENZENE | | 0 | 0 | 0 | 0 | 0 | 0 | 0 | 0 |
| 123TRIMETHYLBENZENE | | 1,666 | 18 | 1,648 | 1,648 | 1 | 1,664 | 1,648 | 1,666 |
| 135TRIMETHYLBENZENE | | 14,435 | 217 | 14,218 | 14,218 | 16 | 14,436 | 14,218 | 14,435 |
| M_XYLENE | | 14,641 | 539 | 14,102 | 14,102 | 52 | 14,589 | 14,102 | 14,641 |
| 13DIETHYLBENZENE | | 0 | 0 | 0 | 0 | 0 | 0 | 0 | 0 |
| 2ETHYL13DIMETHYLBENZENE | | 0 | 0 | 0 | 0 | 0 | 0 | 0 | 0 |
| 1METHYL3PROPYLBENZENE | | 0 | 0 | 0 | 0 | 0 | 0 | 0 | 0 |
| 1ETHYL23DIMETHYLBENZENE | | 0 | 0 | 0 | 0 | 0 | 0 | 0 | 0 |
| 1245TETRAMETHYLBENZENE | | 19,532 | 102 | 19,430 | 19,430 | 6 | 19,526 | 19,430 | 19,532 |
| 1ETHYL24DIMETHYLBENZENE | | 0 | 0 | 0 | 0 | 0 | 0 | 0 | 0 |
| PROPYLBENZENE | | 0 | 0 | 0 | 0 | 0 | 0 | 0 | 0 |
| M_CYMENE | | 0 | 0 | 0 | 0 | 0 | 0 | 0 | 0 |
| SEC_BUTYLBENZENE | | 0 | 0 | 0 | 0 | 0 | 0 | 0 | 0 |
| 1234TETRAMETHYLBENZENE | | 445 | 2 | 443 | 443 | 0 | 445 | 443 | 445 |
| 4ETHYL12DIMETHYLBENZENE | | 0 | 0 | 0 | 0 | 0 | 0 | 0 | 0 |
| P_XYLENE | | 5,590 | 210 | 5,380 | 5,380 | 20 | 5,569 | 5,380 | 5,590 |
| NAPTHALENE | | 0 | 0 | 0 | 0 | 0 | 0 | 0 | 0 |
| BUTYLBENZENE | | 0 | 0 | 0 | 0 | 0 | 0 | 0 | 0 |
| 12DIETHYLBENZENE | | 0 | 0 | 0 | 0 | 0 | 0 | 0 | 0 |
| 2METHYL3PROPYLBENZENE | | 0 | 0 | 0 | 0 | 0 | 0 | 0 | 0 |
| 1235TETRAMETHYLBENZENE | | 5,767 | 28 | 5,738 | 5,738 | 1 | 5,765 | 5,738 | 5,767 |
| PENTAMETHYLBENZENE | | 1,986 | 3 | 1,983 | 1,983 | 0 | 1,986 | 1,983 | 1,986 |
| BICYCLOHEXYL | | 0 | 0 | 0 | 0 | 0 | 0 | 0 | 0 |
| TOTAL | LB/HR | 119,823 | 15,850 | 103,969 | 103,969 | 13,553 | 106,273 | 103,969 | 119,835 |
| ENTHALPY | BTU/LB | -63 | -396 | -158 | -182 | -618 | -179 | -203 | -190 |
| DENSITY | LB/CUFT | 1.33 | 0.24 | 50.49 | 52.01 | 0.23 | 51.57 | 53.47 | 1.77 |
| VOLUMETRIC_FLOW | GPM | 11,253 | 8,393 | 257 | 249 | 7,326 | 257 | 242 | 8,438 |

FIG. 9B

| STREAM NUMBER | | 14 | 15 | 16 | 20 | 26 | 27 | 41 | 51 |
|---|---|---|---|---|---|---|---|---|---|
| TEMPERATURE | DEG F | 95 | 376 | 95 | 331 | 401 | 401 | 392 | 159 |
| PRESSURE | PSIA | 15 | 21 | 15 | 15 | 340 | 340 | 340 | 321 |
| COMPONENTS | MW | | | | | | | | |
| | | | | | | | | | |
| HYDROGEN | | 0 | 0 | 3 | 0 | 0 | 0 | 0 | 3 |
| METHANE | | 0 | 0 | 0 | 0 | 0 | 0 | 0 | 0 |
| WATER | | 0 | 0 | 0 | 0 | 0 | 0 | 0 | 0 |
| ETHANE | | 137 | 0 | 355 | 0 | 0 | 0 | 0 | 492 |
| PROPANE | | 116 | 0 | 71 | 0 | 0 | 0 | 0 | 187 |
| BUTANE | | 232 | 0 | 38 | 0 | 0 | 0 | 0 | 270 |
| TOLUENE | | 4,446 | 0 | 15 | 0 | 0 | 0 | 0 | 4,461 |
| BENZENE | | 0 | 0 | 0 | 0 | 0 | 0 | 0 | 0 |
| O_XYLENE | | 5,364 | 92 | 4 | 92 | 0 | 0 | 0 | 5,459 |
| 124TRIMETHYLBENZENE | | 0 | 31,436 | 0 | 7,142 | 2,429 | 21,863 | 21,863 | 31,436 |
| 1ETHYL2METHYLBENZENE | | 0 | 0 | 0 | 0 | 0 | 0 | 0 | 0 |
| 1ETHYL3METHYLBENZENE | | 0 | 0 | 0 | 0 | 0 | 0 | 0 | 0 |
| 123TRIMETHYLBENZENE | | 0 | 1,664 | 0 | 2 | 166 | 1,497 | 1,497 | 1,664 |
| 135TRIMETHYLBENZENE | | 0 | 14,428 | 0 | 14,291 | 13 | 115 | 115 | 14,428 |
| M_XYLENE | | 14,373 | 1 | 15 | 1 | 0 | 0 | 0 | 14,389 |
| 13DIETHYLBENZENE | | 0 | 0 | 0 | 0 | 0 | 0 | 0 | 0 |
| 2ETHYL13DIMETHYLBENZENE | | 0 | 0 | 0 | 0 | 0 | 0 | 0 | 0 |
| 1METHYL3PROPYLBENZENE | | 0 | 0 | 0 | 0 | 0 | 0 | 0 | 0 |
| 1ETHYL23DIMETHYLBENZENE | | 0 | 0 | 0 | 0 | 0 | 0 | 0 | 0 |
| 1225TETRAMETHYLBENZENE | | 0 | 19,526 | 0 | 0 | 1,953 | 17,573 | 17,573 | 19,526 |
| 1ETHYL24DIMETHYLBENZENE | | 0 | 0 | 0 | 0 | 0 | 0 | 0 | 0 |
| PROPYLBENZENE | | 0 | 0 | 0 | 0 | 0 | 0 | 0 | 0 |
| M_CYMENE | | 0 | 0 | 0 | 0 | 0 | 0 | 0 | 0 |
| SEC_BUTYLBENZENE | | 0 | 0 | 0 | 0 | 0 | 0 | 0 | 0 |
| 1234TETRAMETHYLBENZENE | | 0 | 445 | 0 | 0 | 44 | 400 | 400 | 445 |
| 4ETHYL12DIMETHYLBENZENE | | 0 | 0 | 0 | 0 | 0 | 0 | 0 | 0 |
| P_XYLENE | | 5,563 | 0 | 6 | 0 | 0 | 0 | 0 | 5,569 |
| NAPTHALENE | | 0 | 0 | 0 | 0 | 0 | 0 | 0 | 0 |
| BUTYLBENZENE | | 0 | 0 | 0 | 0 | 0 | 0 | 0 | 0 |
| 13DIETHYLBENZENE | | 0 | 0 | 0 | 0 | 0 | 0 | 0 | 0 |
| 2METHYL1PROPYLBENZENE | | 0 | 0 | 0 | 0 | 0 | 0 | 0 | 0 |
| 1235TETRAMETHYLBENZENE | | 0 | 5,765 | 0 | 0 | 577 | 5,189 | 5,189 | 5,765 |
| PENTAMETHYLBENZENE | | 0 | 1,986 | 0 | 0 | 199 | 1,787 | 1,787 | 1,986 |
| BICYCLOHEXYL | | 0 | 0 | 0 | 0 | 0 | 0 | 0 | 0 |
| | | | | | | | | | |
| TOTAL | LB/HR | 30,430 | 75,335 | 507 | 21,528 | 5,381 | 48,427 | 48,427 | 106,272 |
| ENTHALPY | BTU/LB | -88 | -108 | -1,034 | -103 | -105 | -105 | -111 | -179 |
| DENSITY | LB/CUFT | 52.91 | 45.44 | 0.08 | 46.07 | 44.93 | 44.93 | 45.27 | 51.57 |
| VOLUMETRIC_FLOW | GPM | 72 | 207 | 795 | 58 | 15 | 134 | 133 | 257 |

FIG. 10B

| STREAM NUMBER | | 20 | 99 | 100 |
|---|---|---|---|---|
| TEMPERATURE | DEG F | 331 | 328 | 380 |
| PRESSURE | PSIA | 15 | 15 | 26 |
| COMPONENTS | MW | | | |
| | | | | |
| HYDROGEN | | 0 | 0 | 0 |
| METHANE | | 0 | 0 | 0 |
| WATER | | 0 | 0 | 0 |
| ETHANE | | 0 | 0 | 0 |
| PROPANE | | 0 | 0 | 0 |
| BUTANE | | 0 | 0 | 0 |
| TOLUENE | | 0 | 0 | 0 |
| BENZENE | | 0 | 0 | 0 |
| O_XYLENE | | 92 | 92 | 0 |
| _124TRIMETHYLBENZENE | | 7,142 | 474 | 6,668 |
| _1ETHYL2METHYLBENZENE | | 0 | 0 | 0 |
| _1ETHYL4METHYLBENZENE | | 0 | 0 | 0 |
| _123TRIMETHYLBENZENE | | 2 | 0 | 2 |
| _135TRIMETHYLBENZENE | | 14,291 | 14,068 | 223 |
| M_XYLENE | | 1 | 1 | 0 |
| _13DIETHYLBENZENE | | 0 | 0 | 0 |
| _2ETHYL13DIMETHYLBENZENE | | 0 | 0 | 0 |
| _1METHYL3PROPYLBENZENE | | 0 | 0 | 0 |
| _1ETHYL23DIMETHYLBENZENE | | 0 | 0 | 0 |
| _1245TETRAMETHYLBENZENE | | 0 | 0 | 0 |
| _1ETHYL24DIMETHYLBENZENE | | 0 | 0 | 0 |
| PROPYLBENZENE | | 0 | 0 | 0 |
| M_CYMENE | | 0 | 0 | 0 |
| SEC_BUTYLBENZENE | | 0 | 0 | 0 |
| _1234TETRAMETHYLBENZENE | | 0 | 0 | 0 |
| _4ETHYL12DIMETHYLBENZENE | | 0 | 0 | 0 |
| P_XYLENE | | 0 | 0 | 0 |
| NAPTHALENE | | 0 | 0 | 0 |
| BUTYLBENZENE | | 0 | 0 | 0 |
| _12DIETHYLBENZENE | | 0 | 0 | 0 |
| _2METHYL1PROPYLBENZENE | | 0 | 0 | 0 |
| _1235TETRAMETHYLBENZENE | | 0 | 0 | 0 |
| PENTAMETHYLBENZENE | | 0 | 0 | 0 |
| BICYCLOHEXYL | | 0 | 0 | 0 |
| | | | | |
| TOTAL | LB/HR | 21,528 | 14,635 | 6,893 |
| ENTHALPY | BTU/LB | -103 | -106 | -49 |
| DENSITY | LB/CUFT | 46.07 | 45.90 | 44.86 |
| VOLUMETRIC_FLOW | GPM | 58 | 40 | 19 |

FIG. 11B

| STREAM NUMBER | | 16 | 38 | 48 | 53 | 54 | 73 |
|---|---|---|---|---|---|---|---|
| TEMPERATURE | DEG F | 95 | 148 | 101 | 101 | 101 | 77 |
| PRESSURE | PSIA | 15 | 405 | 320 | 320 | 320 | 405 |
| COMPONENTS | MW | | | | | | |
| HYDROGEN | | 3 | 6,281 | 5,803 | 5,803 | 0 | 478 |
| METHANE | | 0 | 0 | 0 | 0 | 0 | 0 |
| WATER | | 0 | 0 | 0 | 0 | 0 | 0 |
| ETHANE | | 355 | 1,037 | 6,914 | 1,037 | 5,877 | 0 |
| PROPANE | | 71 | 0 | 574 | 0 | 574 | 0 |
| BUTANE | | 38 | 0 | 71 | 0 | 71 | 0 |
| TOLUENE | | 15 | 0 | 48 | 0 | 48 | 0 |
| BENZENE | | 0 | 0 | 0 | 0 | 0 | 0 |
| O_XYLENE | | 4 | 0 | 15 | 0 | 15 | 0 |
| _124TRIMETHYLBENZENE | | 0 | 0 | 31 | 0 | 31 | 0 |
| _1ETHYL2METHYLBENZENE | | 0 | 0 | 0 | 0 | 0 | 0 |
| _1ETHYL4METHYLBENZENE | | 0 | 0 | 0 | 0 | 0 | 0 |
| _123TRIMETHYLBENZENE | | 0 | 0 | 1 | 0 | 1 | 0 |
| _135TRIMETHYLBENZENE | | 0 | 0 | 16 | 0 | 16 | 0 |
| M_XYLENE | | 15 | 0 | 52 | 0 | 52 | 0 |
| _13DIETHYLBENZENE | | 0 | 0 | 0 | 0 | 0 | 0 |
| _2ETHYL13DIMETHYLBENZENE | | 0 | 0 | 0 | 0 | 0 | 0 |
| _1METHYL3PROPYLBENZENE | | 0 | 0 | 0 | 0 | 0 | 0 |
| _1ETHYL23DIMETHYLBENZENE | | 0 | 0 | 0 | 0 | 0 | 0 |
| _1245TETRAMETHYLBENZENE | | 0 | 0 | 6 | 0 | 6 | 0 |
| _1ETHYL24DIMETHYLBENZENE | | 0 | 0 | 0 | 0 | 0 | 0 |
| PROPYLBENZENE | | 0 | 0 | 0 | 0 | 0 | 0 |
| M_CYMENE | | 0 | 0 | 0 | 0 | 0 | 0 |
| SEC_BUTYLBENZENE | | 0 | 0 | 0 | 0 | 0 | 0 |
| _1234TETRAMETHYLBENZENE | | 0 | 0 | 0 | 0 | 0 | 0 |
| _4ETHYL12DIMETHYLBENZENE | | 0 | 0 | 0 | 0 | 0 | 0 |
| P_XYLENE | | 6 | 0 | 20 | 0 | 20 | 0 |
| NAPTHALENE | | 0 | 0 | 0 | 0 | 0 | 0 |
| BUTYLBENZENE | | 0 | 0 | 0 | 0 | 0 | 0 |
| _12DIETHYLBENZENE | | 0 | 0 | 0 | 0 | 0 | 0 |
| _2METHYL1PROPYLBENZENE | | 0 | 0 | 0 | 0 | 0 | 0 |
| _1235TETRAMETHYLBENZENE | | 0 | 0 | 1 | 0 | 1 | 0 |
| PENTAMETHYLBENZENE | | 0 | 0 | 0 | 0 | 0 | 0 |
| BICYCLOHEXYL | | 0 | 0 | 0 | 0 | 0 | 0 |
| TOTAL | LB/HR | 507 | 7,318 | 13,553 | 6,840 | 6,712 | 478 |
| ENTHALPY | BTU/LB | -1,034 | 42 | -618 | -110 | -1,139 | 0 |
| DENSITY | LB/CUFT | 0.08 | 0.14 | 0.23 | 0.12 | 1.71 | 0.14 |
| VOLUMETRIC_FLOW | GPM | 795 | 6,321 | 7,326 | 6,830 | 480 | 420 |

FIG. 12B

| STREAM NUMBER | | 52 | 60 | 65 | 106 | 107 | 108 | 109 | 110 | 111 |
|---|---|---|---|---|---|---|---|---|---|---|
| TEMPERATURE | DEG F | 212 | 466 | 210 | 212 | 466 | 212 | 466 | 212 | 466 |
| PRESSURE | PSIA | 500 | 495 | 15 | 500 | 495 | 500 | 495 | 500 | 495 |
| COMPONENTS | | | | | | | | | | |
| HYDROGEN | LB/HR | 0 | 0 | 0 | 0 | 0 | 0 | 0 | 0 | 0 |
| METHANE | LB/HR | 0 | 0 | 0 | 0 | 0 | 0 | 0 | 0 | 0 |
| WATER | LB/HR | 49,194 | 49,194 | 49,194 | 9,723 | 9,723 | 9,664 | 9,664 | 29,807 | 29,807 |
| ETHANE | LB/HR | 0 | 0 | 0 | 0 | 0 | 0 | 0 | 0 | 0 |
| PROPANE | LB/HR | 0 | 0 | 0 | 0 | 0 | 0 | 0 | 0 | 0 |
| BUTANE | LB/HR | 0 | 0 | 0 | 0 | 0 | 0 | 0 | 0 | 0 |
| TOLUENE | LB/HR | 0 | 0 | 0 | 0 | 0 | 0 | 0 | 0 | 0 |
| BENZENE | LB/HR | 0 | 0 | 0 | 0 | 0 | 0 | 0 | 0 | 0 |
| OXYGEN | LB/HR | 0 | 0 | 0 | 0 | 0 | 0 | 0 | 0 | 0 |
| CARBON_DIOXIDE | LB/HR | 0 | 0 | 0 | 0 | 0 | 0 | 0 | 0 | 0 |
| NITROGEN | LB/HR | 0 | 0 | 0 | 0 | 0 | 0 | 0 | 0 | 0 |
| PENTENE | LB/HR | 0 | 0 | 0 | 0 | 0 | 0 | 0 | 0 | 0 |
| DICYCLOPENTADIENE | LB/HR | 0 | 0 | 0 | 0 | 0 | 0 | 0 | 0 | 0 |
| HEPTENE | LB/HR | 0 | 0 | 0 | 0 | 0 | 0 | 0 | 0 | 0 |
| OCTANE | LB/HR | 0 | 0 | 0 | 0 | 0 | 0 | 0 | 0 | 0 |
| OCTENE | LB/HR | 0 | 0 | 0 | 0 | 0 | 0 | 0 | 0 | 0 |
| NONANE | LB/HR | 0 | 0 | 0 | 0 | 0 | 0 | 0 | 0 | 0 |
| DECANE | LB/HR | 0 | 0 | 0 | 0 | 0 | 0 | 0 | 0 | 0 |
| STYRENE | LB/HR | 0 | 0 | 0 | 0 | 0 | 0 | 0 | 0 | 0 |
| TOTAL | LB/HR | 49,194 | 49,194 | 49,194 | 9,723 | 9,723 | 9,664 | 9,664 | 29,807 | 29,807 |
| ENTHALPY | BTU/LB | -6,683 | -5,593 | -6,686 | -6,683 | -5,593 | -6,683 | -5,593 | -6,683 | -5,593 |
| DENSITY | LB/CUFT | 57.31 | 0.90 | 57.40 | 57.31 | 0.90 | 57.31 | 0.90 | 57.31 | 0.90 |
| VOLUMETRIC FLOW | GPM | 107 | 6,833 | 107 | 21 | 1,351 | 21 | 1,342 | 65 | 4,140 |

FIG. 13B

| STREAM NUMBER | | 71 | 72 | 126 | 127 | 128 | 129 | 130 | 131 | 132 | 133 |
|---|---|---|---|---|---|---|---|---|---|---|---|
| TEMPERATURE | DEG F | 466 | 466 | 466 | 466 | 466 | 466 | 466 | 466 | #N/A | #N/A |
| PRESSURE | PSIA | 495 | 495 | 495 | 495 | 495 | 495 | 495 | 495 | #N/A | #N/A |
| COMPONENTS | | | | | | | | | | | |
| HYDROGEN | LB/HR | 0 | 0 | 0 | 0 | 0 | 0 | 0 | 0 | #N/A | #N/A |
| METHANE | LB/HR | 0 | 0 | 0 | 0 | 0 | 0 | 0 | 0 | #N/A | #N/A |
| WATER | LB/HR | 83,597 | 83,597 | 38,409 | 38,409 | 76,838 | 76,838 | 39,373 | 39,373 | #N/A | #N/A |
| ETHANE | LB/HR | 0 | 0 | 0 | 0 | 0 | 0 | 0 | 0 | #N/A | #N/A |
| PROPANE | LB/HR | 0 | 0 | 0 | 0 | 0 | 0 | 0 | 0 | #N/A | #N/A |
| BUTANE | LB/HR | 0 | 0 | 0 | 0 | 0 | 0 | 0 | 0 | #N/A | #N/A |
| TOLUENE | LB/HR | 0 | 0 | 0 | 0 | 0 | 0 | 0 | 0 | #N/A | #N/A |
| BENZENE | LB/HR | 0 | 0 | 0 | 0 | 0 | 0 | 0 | 0 | #N/A | #N/A |
| OXYGEN | LB/HR | 0 | 0 | 0 | 0 | 0 | 0 | 0 | 0 | #N/A | #N/A |
| CARBON DIOXIDE | LB/HR | 0 | 0 | 0 | 0 | 0 | 0 | 0 | 0 | #N/A | #N/A |
| NITROGEN | LB/HR | 0 | 0 | 0 | 0 | 0 | 0 | 0 | 0 | #N/A | #N/A |
| PENTENE | LB/HR | 0 | 0 | 0 | 0 | 0 | 0 | 0 | 0 | #N/A | #N/A |
| DICYCLOPENTADIENE | LB/HR | 0 | 0 | 0 | 0 | 0 | 0 | 0 | 0 | #N/A | #N/A |
| HEPTENE | LB/HR | 0 | 0 | 0 | 0 | 0 | 0 | 0 | 0 | #N/A | #N/A |
| OCTANE | LB/HR | 0 | 0 | 0 | 0 | 0 | 0 | 0 | 0 | #N/A | #N/A |
| OCTENE | LB/HR | 0 | 0 | 0 | 0 | 0 | 0 | 0 | 0 | #N/A | #N/A |
| NONANE | LB/HR | 0 | 0 | 0 | 0 | 0 | 0 | 0 | 0 | #N/A | #N/A |
| DECANE | LB/HR | 0 | 0 | 0 | 0 | 0 | 0 | 0 | 0 | #N/A | #N/A |
| STYRENE | LB/HR | 0 | 0 | 0 | 0 | 0 | 0 | 0 | 0 | #N/A | #N/A |
| TOTAL | LB/HR | 83,597 | 83,597 | 38,409 | 38,409 | 76,838 | 76,838 | 39,373 | 39,373 | #N/A | #N/A |
| ENTHALPY | BTU/LB | -5,593 | -6,348 | -5,593 | -6,348 | -5,593 | -6,348 | -5,593 | -6,348 | #N/A | #N/A |
| DENSITY | LB/CUFT | 0.90 | 46.62 | 0.90 | 46.62 | 0.90 | 46.62 | 0.90 | 46.62 | #N/A | #N/A |
| VOLUMETRIC FLOW | GPM | 11,612 | 224 | 5,335 | 103 | 10,673 | 206 | 5,469 | 105 | #N/A | #N/A |

FIG. 14B

| STREAM NUMBER | | 66 | 68 | 106 | 107 | 108 | 109 |
|---|---|---|---|---|---|---|---|
| TEMPERATURE | DEG F | 83 | 108 | 212 | 466 | 212 | 466 |
| PRESSURE | PSIA | 50 | 43 | 500 | 495 | 500 | 495 |
| COMPONENTS | | | | | | | |
| HYDROGEN | LB/HR | 0 | 0 | 0 | 0 | 0 | 0 |
| METHANE | LB/HR | 0 | 0 | 0 | 0 | 0 | 0 |
| WATER | LB/HR | 1,170,770 | 1,170,770 | 9,723 | 9,723 | 9,664 | 9,664 |
| ETHANE | LB/HR | 0 | 0 | 0 | 0 | 0 | 0 |
| PROPANE | LB/HR | 0 | 0 | 0 | 0 | 0 | 0 |
| BUTANE | LB/HR | 0 | 0 | 0 | 0 | 0 | 0 |
| TOLUENE | LB/HR | 0 | 0 | 0 | 0 | 0 | 0 |
| BENZENE | LB/HR | 0 | 0 | 0 | 0 | 0 | 0 |
| OXYGEN | LB/HR | 0 | 0 | 0 | 0 | 0 | 0 |
| CARBON_DIOXIDE | LB/HR | 0 | 0 | 0 | 0 | 0 | 0 |
| NITROGEN | LB/HR | 0 | 0 | 0 | 0 | 0 | 0 |
| PENTENE | LB/HR | 0 | 0 | 0 | 0 | 0 | 0 |
| DICYCLOPENTADIENE | LB/HR | 0 | 0 | 0 | 0 | 0 | 0 |
| HEPTENE | LB/HR | 0 | 0 | 0 | 0 | 0 | 0 |
| OCTANE | LB/HR | 0 | 0 | 0 | 0 | 0 | 0 |
| OCTENE | LB/HR | 0 | 0 | 0 | 0 | 0 | 0 |
| NONANE | LB/HR | 0 | 0 | 0 | 0 | 0 | 0 |
| DECANE | LB/HR | 0 | 0 | 0 | 0 | 0 | 0 |
| STYRENE | LB/HR | 0 | 0 | 0 | 0 | 0 | 0 |
| TOTAL | LB/HR | 1,170,770 | 1,170,770 | 9,723 | 9,723 | 9,664 | 9,664 |
| ENTHALPY | BTU/LB | -6,807 | -6,789 | -6,683 | -5,593 | -6,683 | -5,593 |
| DENSITY | LB/CUFT | 61.68 | 61.00 | 57.31 | 0.90 | 57.31 | 0.90 |
| VOLUMETRIC_FLOW | GPM | 2,366 | 2,393 | 21 | 1,351 | 21 | 1,342 |

FIG. 15B

| STREAM NUMBER | | 75 | 76 | 85 | 92 | 93 | 98 | 103 | 104 | 914 |
|---|---|---|---|---|---|---|---|---|---|---|
| TEMPERATURE | DEG F | 105 | 140 | 140 | 105 | 140 | 105 | 105 | 140 | 126 |
| PRESSURE | PSIA | 15 | 14 | 14 | 15 | 14 | 15 | 15 | 14 | 17 |
| COMPONENTS | | | | | | | | | | |
| HYDROGEN | LB/HR | 0 | 0 | 0 | 0 | 0 | 0 | 0 | 0 | 0 |
| METHANE | LB/HR | 0 | 0 | 0 | 0 | 0 | 0 | 0 | 0 | 0 |
| WATER | LB/HR | 0 | 0 | 0 | 0 | 0 | 0 | 0 | 0 | 0 |
| ETHANE | LB/HR | 0 | 0 | 0 | 0 | 0 | 0 | 0 | 0 | 0 |
| PROPANE | LB/HR | 0 | 0 | 0 | 0 | 0 | 0 | 0 | 0 | 0 |
| BUTANE | LB/HR | 0 | 0 | 0 | 0 | 0 | 0 | 0 | 0 | 0 |
| TOLUENE | LB/HR | 0 | 0 | 0 | 0 | 0 | 0 | 0 | 0 | 0 |
| BENZENE | LB/HR | 0 | 0 | 0 | 0 | 0 | 0 | 0 | 0 | 0 |
| OXYGEN | LB/HR | 60,131 | 374,661 | 60,131 | 1,430,390 | 1,430,390 | 374,661 | 712,871 | 712,871 | 7,113 |
| CARBON_DIOXIDE | LB/HR | 0 | 0 | 0 | 0 | 0 | 0 | 0 | 0 | 0 |
| NITROGEN | LB/HR | 226,205 | 1,409,440 | 226,205 | 5,381,000 | 5,381,000 | 1,409,440 | 2,681,750 | 2,681,750 | 23,425 |
| PENTENE | LB/HR | 0 | 0 | 0 | 0 | 0 | 0 | 0 | 0 | 0 |
| DICYCLOPENTADIENE | LB/HR | 0 | 0 | 0 | 0 | 0 | 0 | 0 | 0 | 0 |
| HEPTENE | LB/HR | 0 | 0 | 0 | 0 | 0 | 0 | 0 | 0 | 0 |
| OCTANE | LB/HR | 0 | 0 | 0 | 0 | 0 | 0 | 0 | 0 | 0 |
| OCTENE | LB/HR | 0 | 0 | 0 | 0 | 0 | 0 | 0 | 0 | 0 |
| NONANE | LB/HR | 0 | 0 | 0 | 0 | 0 | 0 | 0 | 0 | 0 |
| DECANE | LB/HR | 0 | 0 | 0 | 0 | 0 | 0 | 0 | 0 | 0 |
| STYRENE | LB/HR | 0 | 0 | 0 | 0 | 0 | 0 | 0 | 0 | 0 |
| TOTAL | LB/HR | 286,336 | 1,784,100 | 286,336 | 6,811,390 | 6,811,390 | 1,784,100 | 3,394,620 | 3,394,620 | 30,538 |
| ENTHALPY | BTU/LB | 7 | 15 | 15 | 7 | 15 | 7 | 7 | 15 | 12 |
| DENSITY | LB/CUFT | 0.07 | 0.06 | 0.06 | 0.07 | 0.06 | 0.07 | 0.07 | 0.06 | 0.08 |
| VOLUMETRIC_FLOW | GPM | 511,580 | 3,470,420 | 536,977 | 12,102,500 | 13,249,400 | 3,187,550 | 6,064,980 | 6,603,180 | 50,391 |

FIG. 16B

| STREAM NUMBER | | 912 |
|---|---|---|
| TEMPERATURE | DEG F | 104 |
| PRESSURE | PSIA | 115 |
| COMPONENTS | | |
| | | |
| HYDROGEN | LB/HR | 0 |
| METHANE | LB/HR | 1,404 |
| WATER | LB/HR | 0 |
| ETHANE | LB/HR | 42 |
| PROPANE | LB/HR | 31 |
| BUTANE | LB/HR | 0 |
| TOLUENE | LB/HR | 0 |
| BENZENE | LB/HR | 0 |
| OXYGEN | LB/HR | 1 |
| CARBON_DIOXIDE | LB/HR | 61 |
| NITROGEN | LB/HR | 45 |
| PENTENE | LB/HR | 0 |
| DICYCLOPENTADIENE | LB/HR | 0 |
| HEPTENE | LB/HR | 0 |
| OCTANE | LB/HR | 0 |
| OCTENE | LB/HR | 0 |
| NONANE | LB/HR | 0 |
| DECANE | LB/HR | 0 |
| STYRENE | LB/HR | 0 |
| | | |
| TOTAL | LB/HR | 1,585 |
| ENTHALPY | BTU/LB | -1,955 |
| DENSITY | LB/CUFT | 0.32 |
| VOLUMETRIC_FLOW | GPM | 609 |

FIG. 17B

| DEALKYLATION SYNTHESIS – FOR DISTILLATION | | | | | C9 Aromatic Steam | | | FOR BLEND |
|---|---|---|---|---|---|---|---|---|
| C₂H₆ Ethane | C₃H₈ Propane | C₆H₆ Benzene | C₇H₈ Toluene | C₈H₁₀ Xylene | CAS# | Chemical Name | Mol% | C₉H₁₂ TMB's |
| X | | | X | | 622-96-8 | 1-ethyl-4-methyl-benzene | 60.292% | |
| X | | | X | | 611-14-3 | 1-ethyl-2-methyl-benzene | 16.172% | |
| X | | | | | 108-67-8 | 1,3,5-trimethyl-benzene | 12.057% | 12.057% |
| | | | X | | 611-14-3 | 1-ethyl-2-methyl-benzene | 5.878% | |
| | | | | X | 108-38-3 | 1,3-dimethyl-benzene | 1.640% | |
| | | | | | 095-63-6 | 1,2,4-trimethyl-benzene | 1.438% | 1.438% |
| | X | X | | | 103-65-1 | propyl-benzene | 1.321% | |
| | X | X | | | 98-82-8 | cumene | 1.010% | |
| | | | | X | 106-42-3 | P-Xylene | 0.133% | |
| | | | | | | Unknown | 0.059% | |
| | | | | | | | 100.000% | |
| -89°C | -42°C | 80°C | 111°C | 135°C | | | | |
| Typical Boiling Points | | | | | | | | |

FIG. 18

| Hydrocarbon | Motor Octane Number (MON) | Paraffin | Aromatic |
|---|---|---|---|
| NONANES (C9) | | | |
| n-Nonane | -20 | Y | |
| 2,2-Dimethylheptane | 63 | Y | |
| 2,2,5-Trimethylhexane | 88 | Y | |
| 2,2-Dimethyl-3-ethylpentane | 112 | Y | |
| 2,2,3,3-Tetramethylpentane | 113 | Y | |
| Iso-Propylbenzene (cumene) | 124 | | Y |
| 1,2,4-Trimethylbenzene (pseudocumene) | 124 | | Y |
| 1,3,5-Trimethylbenzene (mesitylene) | 136 | | Y |
| 2-Phenylpropene | 150 | | Y |
| OTHER AROMATICS PRODUCED | | | |
| Benzene (C6H6) | 90 | | Y |
| Toluene (C7H8) | 112 | | Y |

FIG. 19

| GC/MS C9 Aromatic Stream | |
|---|---|
| 1-ethyl-4-methylbenzene | 52.99% |
| 1,2,4-trimethylbenzene | 22.57% |
| 1,3,5-trimethylbenzene | 11.03% |
| 1-ethyl-2-methylbenzene | 10.17% |
| propyl-benzene | 1.76% |
| 1-methylethyl-benzene | 0.87% |
| 1,2,3-trimethylbenzene | 0.40% |
| p-xylene | 0.07% |
| other | 0.14% |
| | 100.00% |

FIG. 20

| Trimethylbenzenes | Cut | Ratio |
|---|---|---|
| 1,2,4-trimethylbenzene | 22.57% | 66.4% |
| 1,3,5-trimethylbenzene | 11.03% | 32.4% |
| 1,2,3-trimethylbenzene | 0.40% | 1.2% |
| | 34.00% | 100.0% |

FIG. 21

| DEALKYLATION SYNTHESIS – FOR DISTILLATION | | | | |
|---|---|---|---|---|
| $C_2H_6$ | $C_3H_8$ | $C_6H_6$ | $C_7H_8$ | $C_8H_{10}$ |
| Ethane | Propane | Benzene | Toluene | Xylene |
| X | | | X | |
| | | | | |
| X | | | X | |
| | | | | X |
| | X | X | | |
| | X | X | | |
| | | | | |
| | | | | |
| -89°C | -42°C | 80°C | 111°C | 135°C |
| Typical Boiling Points | | | | |

| | C8+C9 Aromatic Steam | Mol% |
|---|---|---|
| CAS# | | |
| 622-96-8 | 1-ethyl-4-methylbenzene | 49.54% |
| 95-63-6 | 1,2,4-trimethylbenzene | 22.57% |
| 108-67-8 | 1,3,5-trimethylbenzene | 11.03% |
| 611-14-3 | 1-ethyl-2-methylbenzene | 9.62% |
| 106-42-3 | p-xylene | 4.07% |
| 103-65-1 | propyl-benzene | 1.76% |
| 98-82-8 | 1-methylethyl-benzene | 0.87% |
| 526-73-8 | 1,2,3-trimethylbenzene | 0.40% |
| | other | 0.14% |
| | | 100.000% |

FIG. 22

| Trimethylbenzenes | Cut | Ratio | Boiling Pt |
|---|---|---|---|
| 1,2,4-trimethylbenzene | 22.57% | 66.4% | 169°C |
| 1,3,5-trimethylbenzene | 11.03% | 32.4% | 165°C |
| 1,2,3-trimethylbenzene | 0.40% | 1.2% | 175°C |
|  | 34.00% | 100.0% |  |

FIG. 23

| CAS# | Trimethylbenzenes (TMB's) | Cut | Ratio | Boiling Pt |
|---|---|---|---|---|
| 95-63-6 | 1,2,4-trimethyl-benzene | 38.174% | 74.889% | 169°C |
| 526-73-8 | 1,2,3-trimethyl-benzene | 7.280% | 14.282% | 175°C |
| 108-67-8 | 1,3,5-trimethyl-benzene | 5.520% | 10.829% | 165°C |
|  |  | 50.974% | 100.000% |  |

FIG. 24

TREATING C8-C10 AROMATIC FEED STREAMS TO PREPARE AND RECOVER TRIMETHYLATED BENZENES

CROSS-REFERENCE TO RELATED APPLICATION

This application claims the benefit of U.S. Provisional Application No. 62/443,292 filed Jan. 6, 2017, which is hereby incorporated by reference.

FIELD OF THE INVENTION

The present invention relates to the preparation of trimethyl benzenes ("TMBs") and other hydrocarbons, as well as fuels and blending components, from heavy aromatic feeds, e.g., C9 aromatic rich streams available from refineries. Of particular interest are higher-octane aromatic compounds such as 1,3,5-trimethyl benzene ("mesitylene") and 1,2,4-trimethyl benzene ("pseudocumene") due to their higher energy density.

BRIEF DESCRIPTION OF THE PRIOR ART

The refining industry currently formulates the motor gasoline pool from a wide range of hydrocarbon streams including $C_4$ to $C_{10}$ saturated branched acyclic alkanes and olefins and monocyclic aromatic compounds. However derived, these latter hydrocarbon streams contain a broad range of components and have usually been distilled, or otherwise treated (e.g., by solvent extraction), to obtain specific desired components or combinations of components. One purpose of these operations in the past has been to obtain high purity, often greater than 99%, chemical feed stocks such as para-xylene and benzene, which have been used in huge quantities in the manufacture of styrene, phenol, polyamide monomers, terephthalic acid and other chemical products. The streams resulting from the separation processes accordingly consist of product streams of benzene, toluene, $C_8$ aromatics containing xylenes, and a bottoms product of $C_9$ and $C_{10}$+ aromatics.

There is extensive knowledge in the refining industry regarding the use of catalysts to restructure molecules for the adaptation of these $C_4$-$C_{10}$ streams. However, these techniques do not satisfy the need for high octane fuels, particularly aviation fuels for piston and turbine engines, which have unique high octane, distillation, flash point, stability and vapor pressure requirements. The prior art primarily has focused on fuels and fuel components that are not able to meet the particularly higher octane demands of unleaded aviation fuel and premium gasolines as measured by Motor Octane Number (MON) which is generally required to be between 80 to 100 MON for most piston engines.

BRIEF DESCRIPTION OF THE DRAWINGS

FIGS. 5A-17A are diagrams showing various portions of an overall process in accordance with the present invention.

FIGS. 5B-17B are tables providing weight balance information for the process streams shown in FIGS. 5A-17A, respectively.

FIG. 18 is a table showing the separation of components of a $C_9$ aromatics pool via isomerization and dealkylation.

FIG. 19 is a table showing the components of a typical $C_9$ stream.

FIG. 20 is a table showing the composition of a $C_9$ aromatic stream.

FIG. 21 is a table showing the ratio of tri-methyl $C_9$-aromatics after hydrodealkylation, transalkylation and isomerization of the $C_9$ aromatic stream of FIG. 20.

FIG. 22 is a table confirming that hydrodealkylation of an aromatic stream comprising $C_8$ and $C_9$ aromatics resulted in the ethyl compounds being converted to toluene and ethane, and the propyl compounds being converted to benzene and propane.

FIG. 23 is a table showing the production of $C_9$'s during the transalkylation process.

FIG. 24 is a table showing that, as a result of the decoupling of the ethyl, propyl and butyls, the fractionating of the trimethyl benzenes is significantly simplified due to the difference in the boiling point of the 1,2,3-trimethyl benzene.

SUMMARY OF THE INVENTION

Figure 1:
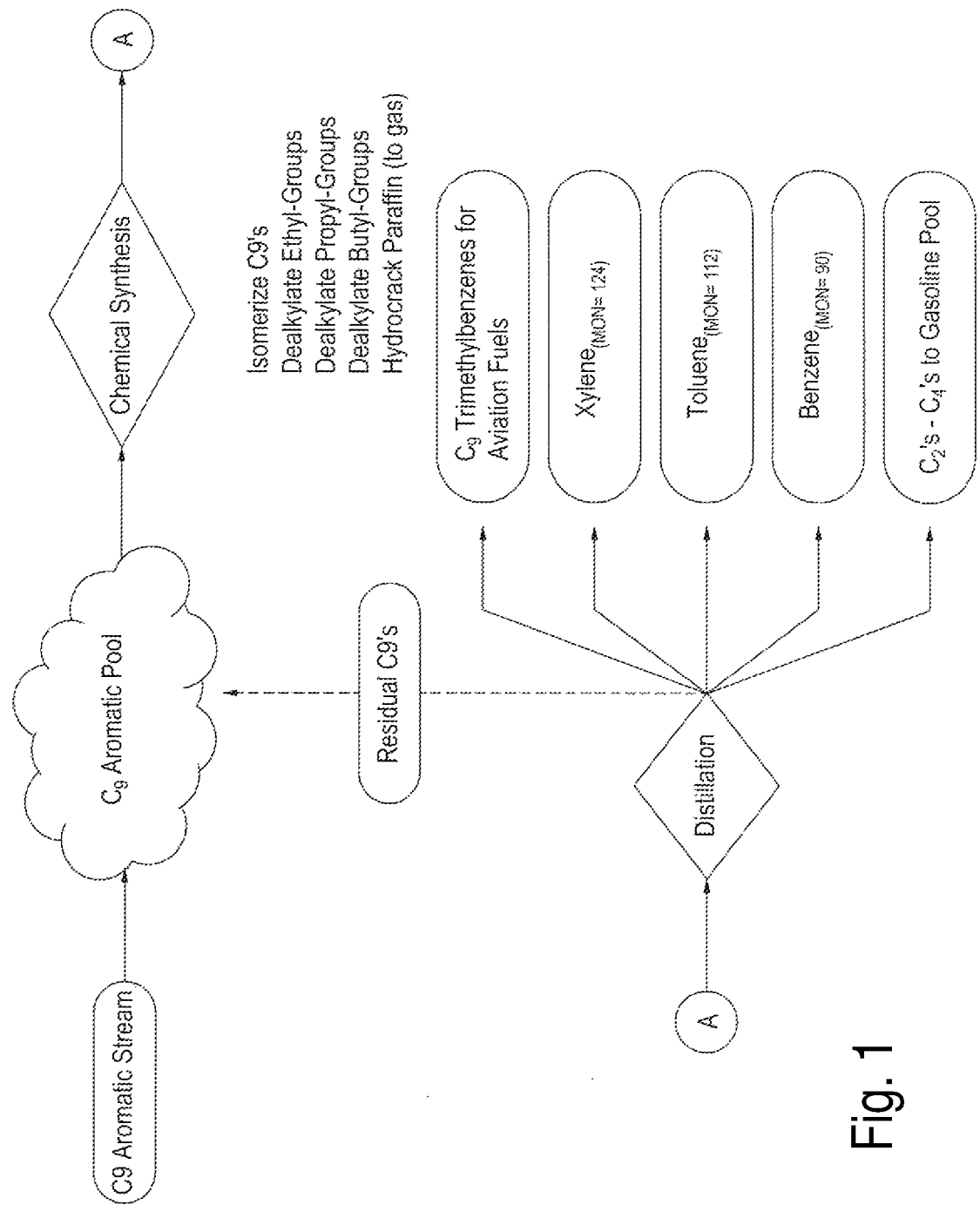
FIGS. 1 and 2 are diagrammatic views of a C9 Stream treatment process according to the present invention.

This invention treats a $C_9$ aromatic blend feed stream to obtain high-octane, TMB-rich products. The process includes any combination of the hydrodealkylation (HDA), transalkylation (TA) and isomerization of the $C_9$ feed to obtain the TMB-rich fraction. The process may also include further treatment to obtain a substantially pure mesitylene product and/or a mixed TMB product comprising mesitylene and pseudocumene. Recovery of other products may also be involved. The invention further comprises the TMB products of these processes.

The invention thereby facilitates the preparation of an unexpectedly high octane aromatic stream, which can serve as a high-octane unleaded fuel or fuel blending component for a wide range of applications, particularly aviation gasoline and other high-performance transportation fuels.

The present invention uses a combination of processing steps to transform a typical mixed-$C_9$ and higher aromatic rich feed stream such as might result from catalytic reforming. Catalytic reforming is frequently followed by a BTX (benzene, toluene, xylene) unit which recovers the light aromatics by extraction, distillation, or a combination of these processes. The aromatics cut left over after the BTX process is generally a $C_9$ and higher aromatic feedstock which can be separated into specific, high octane $C_9$ compounds and mixtures thereof which are isolated and recovered. While some of the individual processing methods have been known in the art, they have not been combined in the manner of the present invention.

These streams are used as a feed stream to the present inventive method. The process uses a catalytic process to transmethylate the $C_8$ and $C_{10}$ methyl aromatics to produce additional $C_9$ trimethyl aromatics. The $C_9$ aromatics are isomerized to increase the amount of the desired TMBs. In addition, certain aromatics are catalytically converted to remove paraffins (to gas) and also to dealkylate the ethyl group from ethyl-methyl-benzene to toluene and ethane, the propyl group from propyl-benzene to benzene and propane, and the butyl group from butyl-benzene to benzene and butane. The remaining blend, which contains predominantly trimethylbenzene isomers, is then distilled to remove the xylene ($C_8$), toluene ($C_7$) and benzene ($C_6$) fractions. $C_2$-$C_4$ components can be returned to the gasoline pool, or recycled within the process. The remaining trimethyl-$C_9$ aromatic stream will have a very high octane suitable as a high-performance unleaded aviation fuel, unleaded aviation fuel blending components or other high-value gasoline blending components.

It is an object of the present invention to provide methods and alternatives for the efficient and cost-effective production of high-octane fuel blends, as well as 1,3,5-trimethyl benzene and pseudocumene fuel products from $C_9$ aromatic feeds. It is a further object of the invention to provide such methods which further provide lower paraffins and $C_6$-$C_8$ aromatics as by-products.

A further object of the present invention is to provide TMB-rich fuel products, with or without pseudocumene, as fuels and fuel blending components.

Further objects, features, aspects, benefits, advantages, and embodiments of the present invention will become apparent from the detailed description and drawings provided herewith.

DESCRIPTION OF SELECTED EMBODIMENTS

For the purpose of promoting an understanding of the principles of the invention, reference will now be made to the embodiments illustrated herein and specific language will be used to describe the same. It will nevertheless be understood that no limitation of the scope of the invention is thereby intended. Any alterations and further modifications of the described embodiments, and any further applications of the principles of the invention as described herein, are contemplated as would normally occur to one skilled in the art to which the invention relates. While certain aspects of the invention are shown in detail, it will be apparent to those skilled in the relevant art that some features that are not relevant to the present invention may not be shown for the sake of clarity.

The present invention provides a surprisingly efficient and cost-effective method for the production of trimethyl benzenes, and particularly 1,3,5-trimethylbenzene (mesitylene), 1,2,4-trimethylbenzene (pseudocumene) and mixtures thereof. In a preferred embodiment, mesitylene is obtained as the primary component of a mesitylene/pseudocumene blend. In another preferred embodiment, mesitylene is obtained as an essentially pure component. These products may be used in a variety of ways, particularly as motor fuels or blending components, including for aviation fuels.

Figure 2:
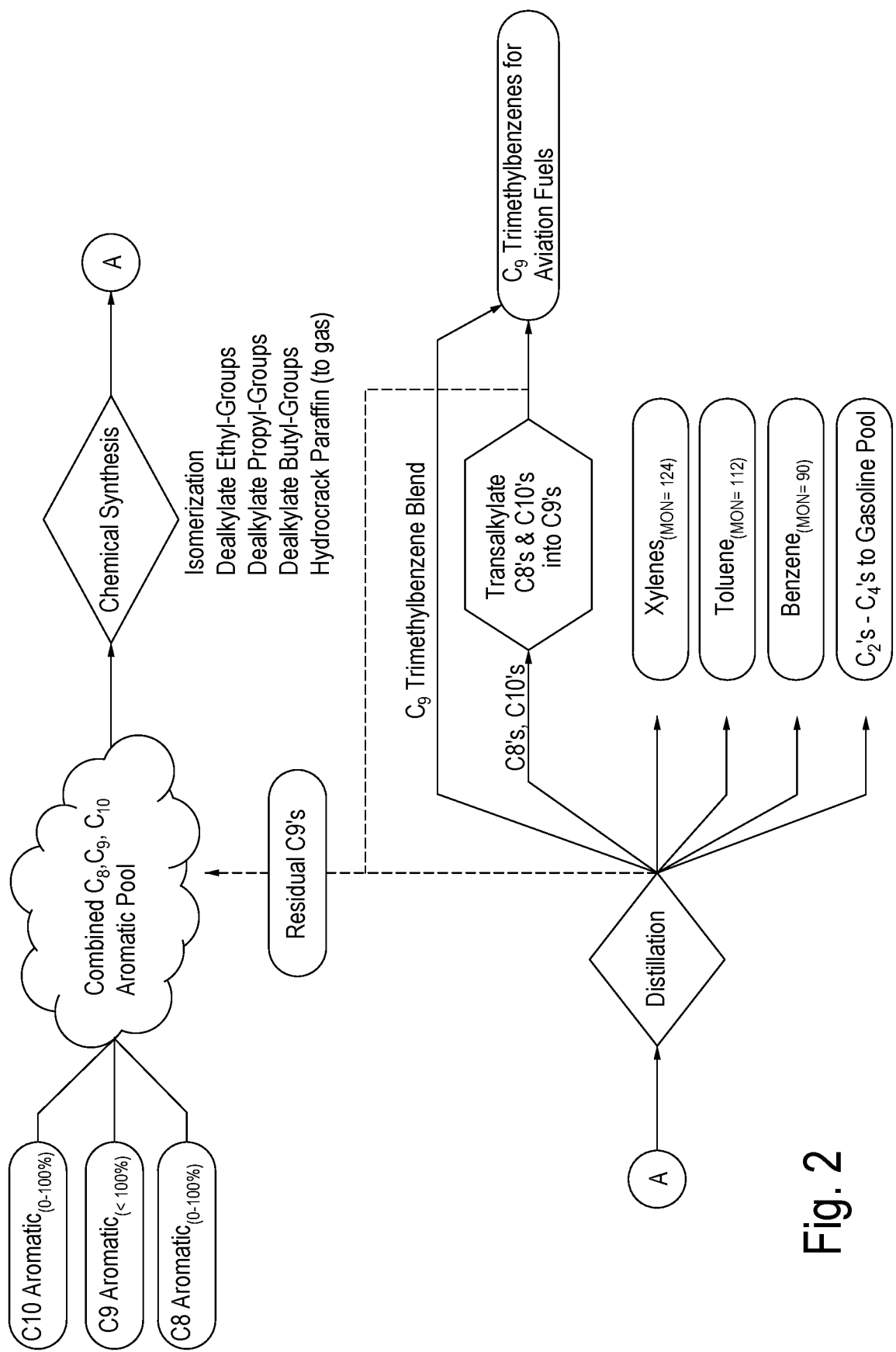

The Overall Process (FIGS. 1 and 2)

The inventive process is directed to the treatment of feed streams which include $C_9$ aromatics in combination with other components. As used herein, the term "C9 Stream" is intended to cover any available aromatic stream, including effluent refinery streams or fractions thereof, which includes a sufficient amount of C9 aromatics to make the process practical. One preferred C9 Stream is a catalytic naptha reformer C9 effluent, particularly after BTX processing.

The C9 Stream may comprise specifically C9 aromatics, e.g., trimethyl-benzenes, ethyl-methyl-benzenes and propyl-benzenes. The stream may also comprise quantities of lower aromatics such as toluene, xylenes, ethylbenzene, etc. The C9 Stream may also include higher aromatics, such as diethylbenzenes, ethyl dimethyl benzenes, methyl propyl-benzenes, tetramethylbenzenes, pentamethylbenzene and various other alkyl benzenes. Of these, the present invention is directed to the preparation and collection of mesitylene, alone or in combination with pseudocumene. This provides a C9 aromatic product which has a much increased MON compared to the initial feed stream. As exemplified hereafter, for example, the present invention can convert a C9 aromatic feed stream having a MON in the order of 96-100, to a C9 product having a MON of 100-108. The result of the present invention is therefore a product which is useful itself as a motor fuel, e.g., an aviation fuel, of high octane, and/or which may be used to blend with gasoline or other components to provide fuels of various octanes as desired.

This invention identifies known molecules within the gasoline blending pool which bring down the average octane rating within the entire motor gasoline pool. This invention seeks to isomerize and catalytically convert certain molecules pooled together across the $C_8$, $C_9$ and $C_{10}$ blend pool known to have very low octane ratings, and further separate certain other molecules in order to derive an unexpectedly high octane of the remaining blended aromatic stream, which could uniquely serve as a high octane blendstock for unleaded aviation fuel and premium gasolines for piston engines.

The $C_9$ aromatics pool shown in FIG. 18 highlights specifically how this invention separates the various compounds via isomerization and dealkylation of the ethyl and propyl groups resulting in ethane, propane, benzene, toluene and xylene, plus trimethylbenzenes that can then be blended to unique recipes to create various grades of high motor octane aviation fuel or premium gasoline.

As shown in FIG. 1, the inventive process starts with a C9 Stream which is chemically treated, alone or in combination with recycle or other feed streams. The treatments provide hydrodealkylation of ethyl, propyl and butyl groups, and transalkylation and isomerization of the C9's, to yield an effluent "A". This process is followed by one or more steps which treat the "A" stream to allow separate collection of the desired C9 trimethylbenzene products. These further separation steps may also provide for the separate collection of xylenes, toluenes, benzene, light hydrocarbons, and hydrogen. The overall process provides a suitable yield of the desired trimethylbenzene products, as well as providing various other product streams that have value in gasolines and for other products and purposes. In the more complex embodiment shown in FIG. 2, the C9 Stream includes significant amounts of other aromatics. In this embodiment, there is increased effect of the dealkylation, isomerization and transalkylation, as further described hereafter.

C9 Aromatic Feed Streams

In the simplest form of the invention, the C9 Stream contains primarily C9 and higher components, and the process involves several steps for converting the C9 components to mesitylene and pseudocumene, particularly mesitylene. However, while a high concentration of C9 aromatics in the feed stream may be preferred, it will be appreciated that the C9 feed may also include a variety of C7-C12 components including paraffins. Examples of typical feed streams are provided elsewhere herein. The present invention applies a number of processes which convert these various components of a C9 feed stream to a high yield of the desired blendstock, including the increased yield of mesitylene and pseudocumene.

One process is hydrodealkylation, which selectively removes the ethyl and propyl constituents of the aromatics, while leaving the methyl constituents. A second process is isomerization, which is performed, for example, to convert 1,2,3-trimethyl benzene to the desired mesitylene and pseudocumene. Conversion to mesitylene, and/or pseudocumene, may also occur for the hydrodealkylated C9 components. Thus, a third reaction which may occur is transalkylation, which is the reaction of light (C7 and C8) and heavy (C10, C11 or C12) methylbenzenes into trimethylbenzenes, including pseudocumene and mesitylene. Optionally, saturated hydrocarbons that may be present in the feed stream will be hydrocracked into lower alkanes, which can be used as a higher-octane blendstock, or further processed and optionally separated by distillation.

A significant advantage of the present invention is that it is operable with aromatic feeds which are readily available, for example from catalytic reforming of heavy naphtha. A number of proprietary catalytic reforming processes are available, but they possess many features in common. The purpose of catalytic reforming is to increase the octane number of a refinery stream, primarily by converting the naphthenes to aromatics and the paraffins to more branched structures. Typically, feed stocks are rich in paraffins and naphthenes with some aromatic content, and product streams are somewhat reduced in paraffin content, but significantly reduced in naphthenes. Aromatics are usually the largest component of catalytic reformate. Depending on the refinery processes and the feed stocks available, different degrees of reaction severity may be chosen to maximize the yields of high-octane blendstocks. Furthermore, this process seeks to optimize the refinery options involving process severity and catalyst life, limiting volume loss, and maximizing yield of higher octane blendstocks. This process can also be tailored to minimize any benzene byproducts to fall well within the regulatory limits for gasoline blending.

Although catalytic reforming is a net hydrogen producer, some hydrogen is typically recycled to the feed to help minimize coking. This invention may use excess (impure) hydrogen from the reformer in which case no hydrogen separation may be required. Reactors in this invention are typically fixed bed units, or they may employ continuous catalytic regeneration. The net reaction is endothermic. Heat may be supplied by a process furnace. There may be multiple passes through the furnace and multiple separate catalyst beds.

Although catalytic reforming processes differ in the catalyst formulations used, all current processes use precious Pt group metals. Because precious metal catalysts are subject to poisoning, feed to catalytic reforming is typically treated to remove sulfur compounds and other catalyst poisons. Operation may be described as continuous, cyclic or regenerative; these terms are descriptive of equipment configurations designed to permit replacement and/or regeneration of catalyst without complete unit shutdown. This is an important consideration because reforming catalysts tend to become fouled over time by the deposition of coke, although they can be regenerated by oxidation. A fuller discussion of catalytic reforming can be found in Antos, G. J. and Aitani, A. M., "Catalytic Naphtha Reforming" Marcel Dekker (2004); and Rahimpour, M. R. et al., "Progress in Catalytic Naphtha Reforming Process: A Review", Applied Energy, v109, pages 79-93 (2013).

Such feeds are the result of the typical naptha reformate process, for example, and may include a variety of other aromatic components, as well as non-aromatic components such as alkanes. Typical refinery C9 fractions may include a variety of C7-C10 components. For example, heavy reformate typically contains significant amounts of C10 and higher aromatics. Heavy reformate may be treated by distillation to remove the C O's and heavier components, yielding "fractionated heavy reformate." Benzene, toluenes and xylenes may be removed through a conventional BTX process, which sometimes has already been carried out by the refinery before the C9 fraction is isolated. The concentration of C9 aromatics in the feed will depend on the processing of the feed prior to its use in the present invention.

It is a significant advantage of the present invention that the process uniquely combines several types of treatments which effectively eliminate or convert these various feed streams to the desired C9 product(s) in high proportion.

Table 1 lists typical constituents of a heavy reformate feed useful with the present invention.

TABLE 1

Composition of heavy reformate feedstock.

| Major compound | Short name | wt. % |
|---|---|---|
| Iso-propyl benzene | iPB | 1.7 |
| n-Propyl benzene | nPB | 4.3 |
| 1-Methyl 2-ethyl benzene | 1M2EB | 6.5 |
| 1-Methyl 3-ethyl benzene | 1M3EB | 18.5 |
| 1-Methyl 4-ethyl benzene | 1M4EB | 9.1 |
| 1,2,3-Tri-methyl benzene | 123TMB | 6.6 |
| 1,2,4-Tri-methyl benzene | 124TMB | 39.1 |
| 1,3,5-Tri-methyl benzene | 135TMB | 10.1 |
| Total $A_9$ | | 95.9 |
| n-Butyl benzene | nBB | 0.5 |
| 1,4-Diethyl benzene | 14DEB | 0.8 |
| 1,3-Diethyl benzene | 13DEB | 0.4 |
| 1,3-Dimethyl, 5-ethyl benzene | 13DM5EB | 0.8 |
| 1,4-Dimethyl, 2-ethyl benzene | 14DM2EB | 0.4 |
| Others $A_{10}$ | | 1.2 |
| Total $A_{10}$ | | 4.1 |

Hydrodealkylation

The present invention includes the hydrodealkylation (HDA) of certain aromatic compounds that may be present in the $C_9$ aromatic feed. The process is carried out under conditions which do not cleave the substituent methyl groups, but will selectively remove the higher $C_2$-$C_4$ alkyl substituents, as their corresponding alkanes, thus converting the higher ($C_2$+) alkyl benzenes to leave only a mix of benzene and methylated benzenes as the aromatic constituents. For example, ethyl toluene is converted to ethane and toluene, propyl benzene is converted to propane and benzene, and butyl benzene (a $C_{10}$ compound) is converted to butane and benzene. The consequence of the HDA process is therefore the production of, inter alia, benzene, toluene and polymethyl benzenes, including xylenes, as well as certain lower alkanes. It may be of particular interest to remove xylenes at this point, which will be without ethylbenzenes, as these are more valuable to refineries than normal C8 compounds.

HDA is preferably operated at a relatively higher temperature (than the TA) of above 250-300° C. However, under these harsher conditions there may be some transalkylation and isomerization that takes place. As later discussed, in one embodiment the HDA effluent is treated to remove light ($C_{6-8}$) aromatics, prior to the subsequent lower temperature TA. The light aromatics at this stage will overall have a lower ratio of methyls to aromatics, and the removal enhances the TA process, if utilized.

Transalkylation

The transalkylation (TA) and isomerization step results in a redistribution of methyl groups among the aromatics. Any of the $C_6$-$C_{10}$ aromatics may be affected by TA. Thus, a $C_8$ aromatic may add a methyl group or a $C_{10}$ may give up a methyl group—each resulting in formation of a TMB. The present invention combines HDA and TA with correlated recycle and recovery steps to obtain a high yield of mesitylene. Conditions for providing the TA and isomerization are known in the art. In a preferred embodiment, the TA is conducted at a relatively lower temperature (than the HDA) of less than 250° C. in order to favor higher-octane TMB production.

One aspect of this process, therefore, involves taking advantage of the known equilibrium distribution of trimethyl benzenes in an aromatic pool. Egan describes aspects of the equilibrium distribution of methylbenzenes in transalkylation. See, Egan, Clark J., "Calculated Equilibria of the Methylbenzenes and Benzene from 298° to 1000° K", J. Chem. And Eng. Data 5 (3) 298, July 1960, hereby incorporated by reference in its entirety. The present process includes selectively recovering the mesitylene, by itself or optionally with the pseudocumene, from the equilibrium pool of the $C_9$ and other isomers.

As known in the art, a relevant parameter in transalkylation is the ratio in the feed stream of methyl groups to benzene groups. Egan shows, for example, that the equilibrium mesitylene concentration (as well as the pseudocumene concentration) peaks at a methyl/benzene ratio of 3.0. It is therefore a preferred embodiment of the present invention, though not a requirement, to operate the transalkylation step with a methyl/benzene ratio of the feed close to 3.0. This is readily accomplished, for example, by recycling tetra and higher methylbenzenes from a subsequent process stream. Note that these higher alkylbenzenes need only be present at the final transalkylation step and need not flow through the multi-stage hydrodealkylation system.

In some embodiments, HDA may be a relatively severe process which may be performed at higher temperatures. Consequently, TA and isomerization can occur automatically during HDA. However, redoing TA at conditions suitable to maximize mesitylene, generally at lower temperatures, provides a higher yield.

A refiner wanting to produce a lot of mesitylene will choose reformate streams having a higher starting methyl/benzene ratio, and will then convert xylenes to C9 aromatics in the HDA stage. Refiners can add a splitter at low cost to an existing tower to get the higher M/B ratios. Alternatively, a refiner may choose reformate streams with lower starting M/B ratios, and then perform HDA/TA to make mesitylene and also make more xylenes without ethylbenzenes due to the hydrodealkylation.

The sequential operation of the HDA and TA processes provides a desirable result in the production of the TMBs. The HDA is preferred to operate at a higher temperature, for example, above 250° C. The HDA reactions do not affect the M/B ratio, and the effluent thus has the same ratio as the initial feed. However, as discussed with respect to an alternate embodiment, the HDA effluent may be treated to remove the light aromatics, thereby increasing the M/B ratio of the feed to the TA reaction unit.

To maximize the yield of 1,3,5-trimethyl-benzene using the TA process, it is necessary to distill mesitylene and recycle the heavy compounds, thereby increasing the pool of feedstocks to TA with a higher ratio of methyl-benzenes. This process follows the equilibrium law of Le Chatelier's principle.

Sample HDA/TA Processes

The HDA/TA process is generally understood in the art. It provides for the removal of $C_2$ and higher alkyl groups from the aromatics of the $C_9$ Stream, and an equilibrium distribution of the methyl groups among the aromatics. An example of a conventional combined HDA/TA process is described in detail in U.S. Pat. No. 4,172,813, which is hereby incorporated by reference in its entirety. As described in the '813 patent, for example, the feed is contacted with a suitable catalyst in the presence of a hydrogen-affording gas. The '813 patent describes a TMB stream which is an equilibrium mixture of $C_9$ methyl aromatics with essentially all higher alkyl groups removed. The feed stock contained 65% toluene with the balance C9 and higher aromatics. Close to equilibrium results are obtained at 800-900° F. and 172 PSIG at a WHSV of 3.7 or 3.8 $hr^{-1}$. Excess hydrogen for the dealkylation reaction was provided; the examples use just over 1.7:1 of H2:hydrocarbon. Various operating conditions are selected to suit the catalyst, which may include particular molar ratios of hydrogen to hydrocarbon, not including inert, gas phase hydrocarbons. Excess hydrogen purity of 70% from the refinery is acceptable. Operating pressures, temperatures and contact times are also selected in accordance with known operation of these types of catalysts.

Catalysts

An example of a suitable catalyst is a metal and zeolite operated at temperatures from 200-1000° C., pressures from 1-100 atmospheres and a space velocity from 0.1-10 $hr^1$. The catalyst metals include, Pt, Pd, Re, Rh, Ir and Mo. These may be present as an oxide, metallic or alloy nano-particles. The preferred metals are Pt, Re and Mo. The metal loadings can be from 0.05 to about 10 weight % as metal in the catalyst. The metals are typically supported on a high surface area support such as alumina, silica, and other refractory oxides. These oxides provide high surface area, porosity and physical strength. The oxide support also contains an acidic form of zeolite Y (FAU), beta (BEA), mordenite (MOR), ZSM-5 (MFI). The amount of zeolite may be from about 10% to 90% of the oxide support. For C9 aromatic feeds, large pore zeolites are preferred, including zeolite Y (FAU), mordenite (MOR) and beta (BEA). The preferred catalyst(s) depend upon the configuration of the invention and the processing options chosen for a specific refinery configuration.

The combined process of HDA and TA thus treats the C9 components in a manner to increase the proportion of desired mesitylene and pseudocumene, while converting other likely present components to readily eliminated compounds. Hemimellitene, 1,2,3, trimethylbenzene, is the most difficult component to separate by distillation from mesitylene and pseudocumene. Fortunately, as shown by Egan, the equilibrium concentration of hemimellitene is always quite low. The ethyl toluenes which have a boiling point close to that of mesitylene are eliminated by removing the ethyl groups in the HDA process. This is important because unlike ethyl toluenes, the boiling point of toluene is sufficiently different that it is readily separated from mesitylene (and pseudocumene) by distillation. The process therefore preferably removes at least 75%, and more preferably at least 90%, of the ethyl toluenes in the HDA step. As a result, all components present following the HDA/TA processes are readily separated from the mesitylene and pseudocumene. For example, the benzene, toluenes and xylenes, if not converted to the desired trimethyl benzenes, can be removed through a conventional BTX tower. The lower alkanes and hydrogen are easily separated in a conventional manner prior to the BTX tower, and could even be removed prior to the TA unit when operated separately from the HDA reactor.

Hydrocracking

As has been previously described, many refineries practice high severity catalytic reforming and some follow this operation with what is known in the art as a BTX extraction unit to recover the light aromatics valuable as chemical feed stocks. In this scenario, the reformer effluent contains a relatively low concentration of light paraffins which are conveniently removed prior to the BTX unit. BTX raffinate is heavy aromatics suitable for feed to the present invention.

If a significant amount of paraffins are present in the C9 Stream, the process preferably includes the step of hydrocracking. Hydrocracking is well known in the art and occurs under the same reaction conditions as HDA and TA. Alkanes and cycloalkanes are cracked into lower molecular weight alkanes, which are separated by phase separation (degassed) or by distillation for use as a high-octane blendstock or for subsequent processing.

BTX

Table 2_provides a typical effluent composition from a low severity catalytic reformer. This stream may be fed directly into the process of the present invention. The majority of the paraffin components will pass through both the HDA and TA reactions unreacted, although the heavier paraffins (e.g. C10, C9, etc.) are likely to hydrocrack as part of the process. Transalkylation effluent can then conveniently be fed to a BTX unit whose raffinate will be a mixture of C9 and higher methyl aromatics. A pseudocumene/mesitylene mixture is readily recovered from this stream (and can be further processed to obtain pure mesitylene), leaving a higher aromatics stream suitable for recycle to transalkylation.

TABLE 2

| | |
|---|---|
| C5 paraffin | 0.272 |
| C6 paraffin | 0.04 |
| C 7 paraffin | 0.041 |
| C8 paraffin | 0.053 |
| C9 paraffin | 0.033 |
| C10 paraffin | 0.007 |
| Naphthenes | 0.01 |
| Benzene | 0.009 |
| Toluene | 0.136 |
| C8 aromatics | 0.274 |
| C9 aromatics | 0.126 |
| Total | 1.001 |

Alternatively, if the hydrodealkylation and transalkylation reactions are carried out in separate reactors, the BTX unit can be positioned between the HDA and TA steps. In this case, a simple BTX distillation can remove $C_6$-$C_8$ components formed in the HDA effluent. As above, a pseudocumene/mesitylene mixture can be recovered from TA by distillation and the heavier aromatics can be recycled.

Many commercial proprietary BTX extraction systems are available and are known by trade names such as Udex and Tetra. Solvents such as higher ethylene or propylene glycols or sulfolane are employed. Any of these systems are suitable for use as above described.

The Process in Detail

The present invention has been shown diagrammatically in FIGS. 1 and 2. These diagrams indicate an overall process involving HDA and TA processes, combined with recycle of certain components, which increase the concentration of mesitylene over that present in the initial C9 Stream. This process generally involves several conventional steps which are combined in a unique manner, with other process methodology, to produce a high-octane product which is rich in TMB. A more specific exemplary process is described hereafter, but it will be appreciated that certain aspects of the described process may be varied as understood by those skilled in the art. For example, the following description provides separate HDA and TA reactors, but it is within the skill in the art to operate such reactors so as to achieve concurrent HDA and TA within individual reactors.

Figure 3A:
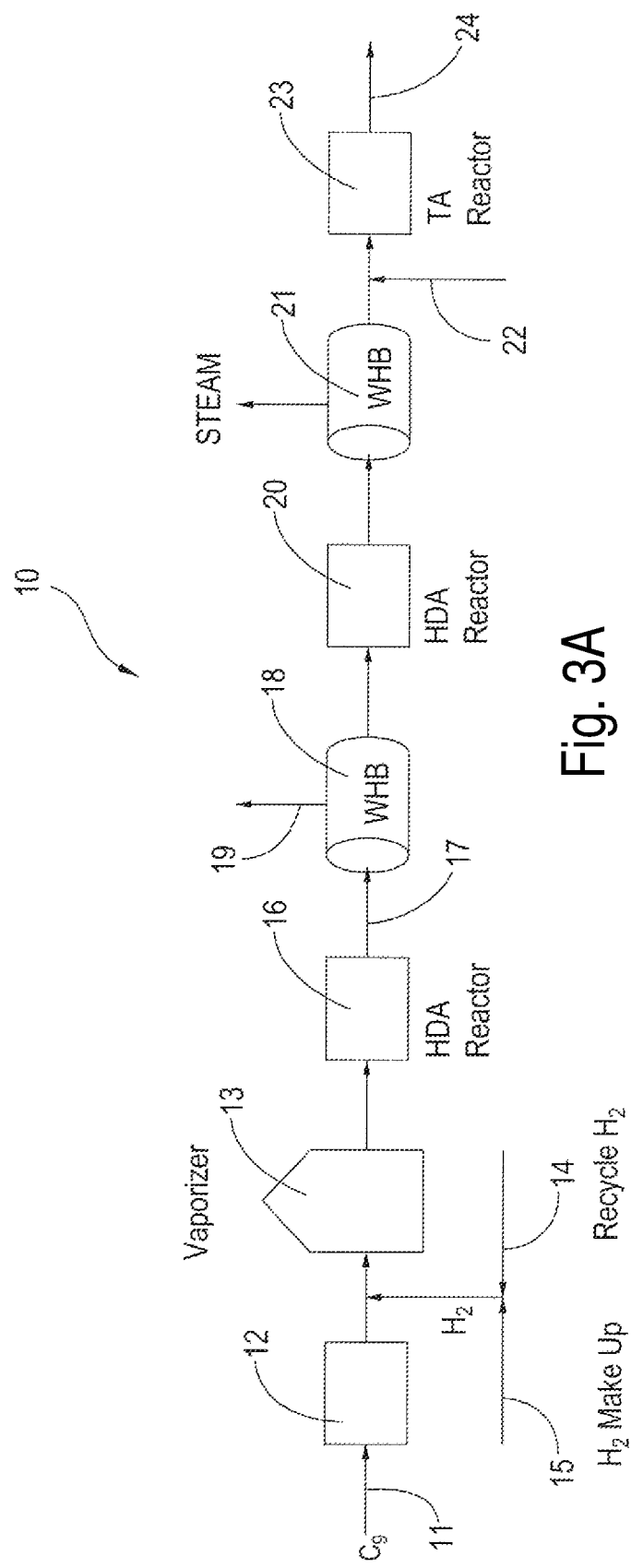
FIGS. 3A and 3B are flow diagrams showing typical major components of a process according to an embodiment of the present invention.

Referring to FIG. 3A, there is shown a preferred embodiment of a process 10 according to the present invention. In general, the feed stock is treated using one or more adiabatic reactors operating at conditions to perform the HDA/TA processes, as generally known. The use of multiple reactors, with intermediate heat removal to steam (or cooling water), facilitates control of the exothermic HDA reactions. HDA can also be carried out in an isothermal reactor wherein the catalyst is contained in tubes and a heat transfer fluid on the shell side removes the heat. Typical heat transfer fluids are Dowtherm and other heat transfer oils or high pressure steam. It is also well known in the art to place the catalyst on the shell side of an isothermal reactor and the heat transfer fluid in the tubes. Cold shot cooling can also be employed. In this embodiment, instead of recovering the heat to steam in between reactor stages, additional cold hydrogen or other inert gas or liquid component is added between stages.

Typically, the C9 Stream is mixed with a hydrogen-containing gas and preheated to a suitable temperature, and then transferred to the hydrodealkylation/transalkylation reaction zone. Besides being a reactant, the hydrogen also provides dilution of the hydrocarbon stream and limits the adiabatic temperature rise across each reaction stage. It will be clear to one of skill in the art that the hydrogen can be replaced in part (only in part because the hydrogen is reactant as well as diluent) by a gas inert in the reaction such as nitrogen or a lower hydrocarbon such as methane, ethane or propane or mixtures thereof or mixtures thereof further comprising hydrogen or nitrogen. As described hereafter, many of these components can be obtained from other byproduct streams. As shown in FIG. 3A, the C9 Stream 11 is provided to booster pump 12 which elevates the liquid to a reaction pressure, e.g., 400 PSIA, before the stream enters vaporization furnace 13. Hydrogen recycle 14 from a subsequent separation step is preferably combined with make-up hydrogen 15 and passes through a separate coil in furnace 13. These gas phase streams combine before entering the first stage reactor 16. Effluent 17 enters a waste heat boiler 18 where it is cooled by generating 750 PSI steam 19. A second stage reactor 20 and boiler 21 are preferably included, and one or more additional stages (not shown) may be added. In this embodiment, effluent from the last of the HDA stages is mixed with a C9 and higher aromatics recycle stream 22 (from a subsequent separation section) before being fed to a transalkylation reactor 23, which yields effluent stream 24.

Figure 3B:
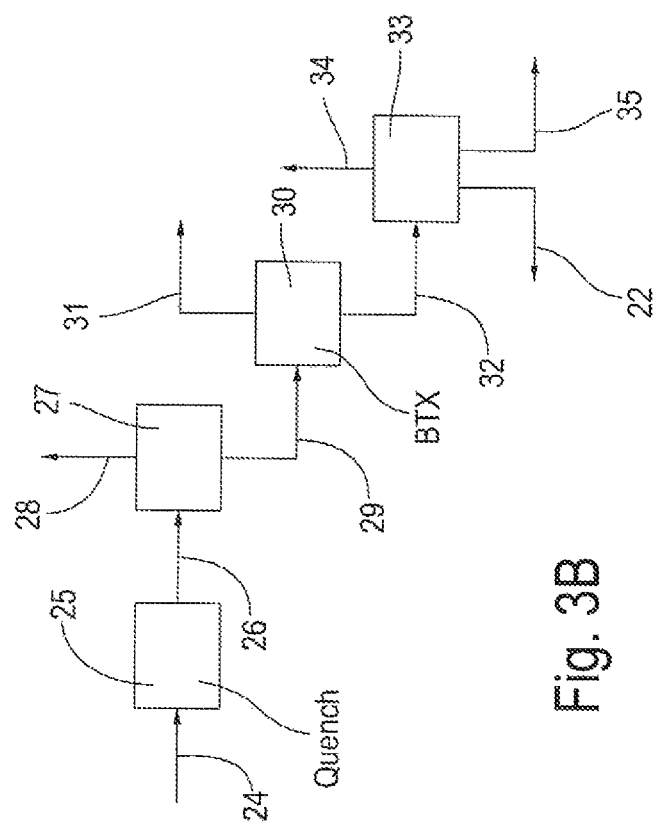

As shown in FIG. 3B, the effluent 24 from the HDA/TA reactor(s) is fed to a quench column 25 which cools the material. This cooled material is then fed through line 26 to a partial condensation unit 27. The lighter components comprising C2-C4 paraffins and hydrogen are removed by way of line 28 and the heavier components comprising C6-C10 and higher aromatics are removed through line 29, and may be recycled to the TA reactor, as elsewhere described. Alternatively, the quench column overheads can be fed to an absorption or extraction unit to separate the hydrogen from the light hydrocarbons. The heavier components in line 29 are then fed into a conventional type BTX (benzene/toluene/xylene) column 30. The BTX column separates out through line 31 the toluenes, xylenes, and benzene from the C9 and higher aromatics.

The bottoms 32 from the BTX column pass to the product column 33 which takes the desired mesitylene/pseudocumene product overhead 34 from a bottoms including some pseudocumene and higher polymethylbenzenes. Pseudocumene distributes between the overheads and bottoms of this column. A purge 35 of C10 and higher aromatics is taken from the bottoms of this column to prevent unreactive heavy compounds from building up. The balance of the higher polymethylbenzenes is recycled to the transalkylation unit by way of line 22 (FIG. 3B). It is unnecessary to send these aromatic heavies to the HDA reactors.

The lighter component overheads 28 from quench column 27 may also be processed for recovery of the lighter components. Most of the $C_3$ and $C_4$ is removed against cooling water and the residual gasses pass to an ethane chiller (not shown) where the ethane is condensed against chilled brine at about $-5°$ C. Uncondensed hydrogen is recompressed to reaction pressure and recycled through line 14 (FIG. 3A). H2 may also be combined with $C_2$-$C_4$ components as previously mentioned.

Figure 4:
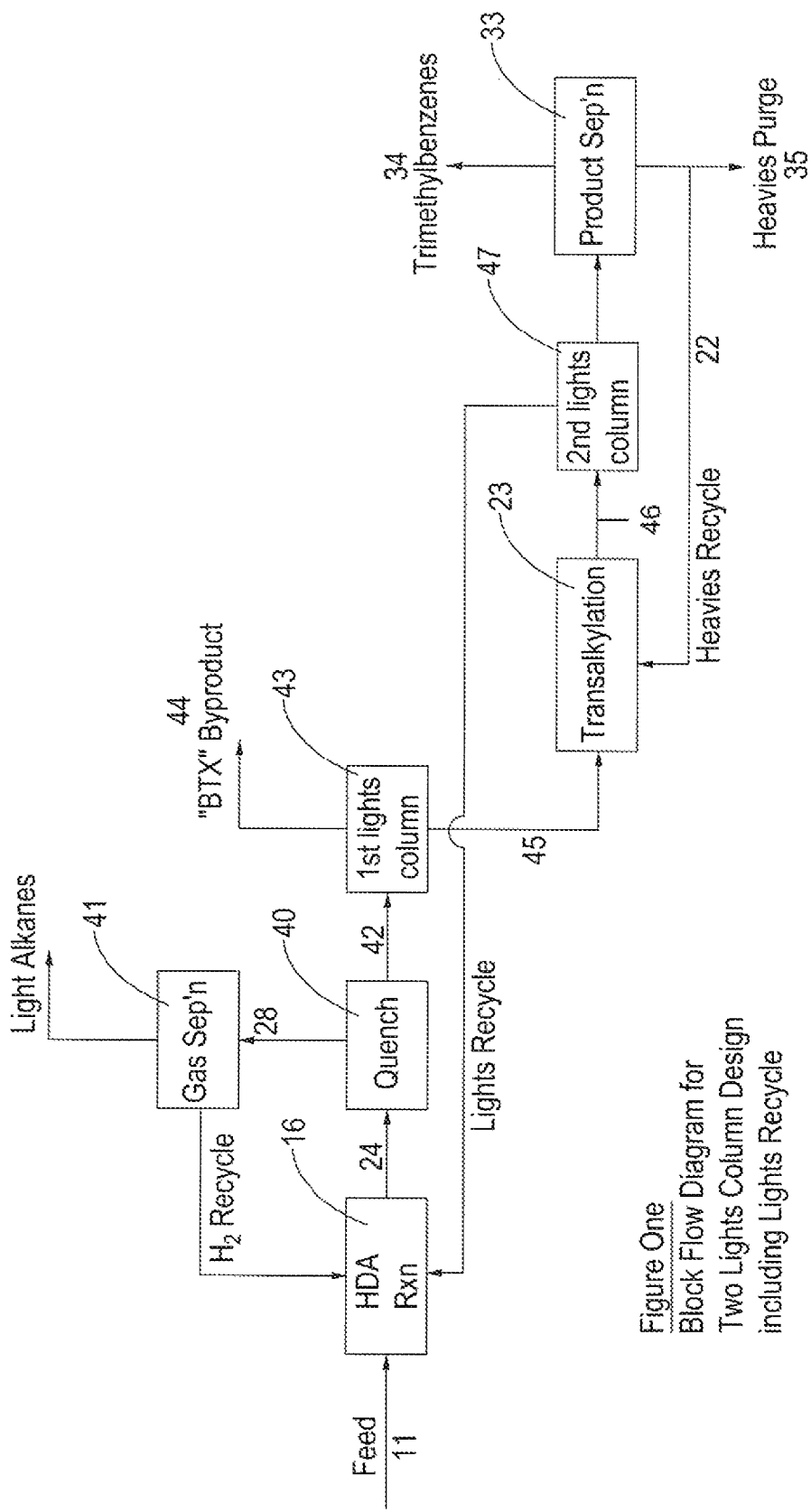
FIG. 4 is a flow diagram showing an alternate embodiment of the present invention.

The foregoing description provides a system in which the aromatic lights are removed by means of a BTX column 30 (FIG. 3B), which is positioned after the TA reactor. In that embodiment, the HDA effluent is shown as entering the TA reactor (FIG. 3A) without processing out the aromatic lights. Referring to FIG. 4, there is shown an alternate embodiment in which two separate lights separations are made. As in the earlier embodiment, the feed stream 11 is fed to the HDA reactor 16. In contrast, this embodiment then directs the HDA effluent 24 to a quench column 40, where the H2 and light alkanes are separated out by gas separator 41.

The remaining liquid 42 from the HDA effluent is fed to a first aromatic lights column 43 and the benzene and toluene, and perhaps some xylenes 44 are collected out. Given the limited methyl/benzene ratio for benzene and toluene, it is most productive to remove these components, as compared to the xylenes. Regardless, removal of any of these components can significantly move the equilibrium composition coming out of the TA reactor to higher methylated benzene compounds, including the desired TMBs. This is because the BTX removal occurs at a point where the methyl/benzene ratio is desirably lower than it may be elsewhere. Further, the removal of these components raises the methyl/benzene ratio of the remaining liquid 45, which is then fed to the TA reactor 23. The TA effluent 46 is transferred to a second lights column 47, where any remaining C6-8 compounds are removed. The remaining bottoms material is processed in a product column 33 as previously described.

This embodiment further provides for the recycle of several byproduct streams. As shown in FIG. 4, the H2 recovered in gas separator 41 may be recycled to the HDA reactor as needed. At least a portion of the heavy aromatic bottoms from the product column 33 is combined with the feed to the TA reactor in order to increase the methyl/benzene ratio for transalkylation. A purge of some amount of the heavies is appropriate to prevent a buildup of such materials in the product column. In addition, the BTX light aromatics may be recycled to the HDA reactor to provide additional aromatics for re-equilibration at high temperature.

In one embodiment the combined processes of HDA and TA with distillation and recycling described herein yield a high-octane, TMB-rich product containing primarily mesitylene (1,3,5-trimethyl benzene), and some amount of pseudocumene. As used herein, the term "TMB-rich" after distillation and recycling refers to a C9 aromatic product containing at least about 50 wt % mesitylene, preferably at least 60 wt % mesitylene and more preferably at least 70 wt % mesitylene. Other embodiments produce high-octane blendstocks that are TMB-rich product whereby the TMB compounds are in higher proportion than the original feedstock; these are well suited for use as a premium motor fuel blendstocks, and aviation fuel, either as it is obtained or after blending with other components. In particular, the presence of the mesitylene provides a desirably high MON and other characteristics suitable for such fuels. It is an additional advantage of the present invention that the inventive process provides TMB-rich products which have this utility in the absence of TEL and aromatic amines.

The process may optionally include a further purification of the TMB-rich product to obtain a Substantially Pure Mesitylene product, which refers to a product that is at least about 90 wt % mesitylene, and preferably at least 95 wt % mesitylene. To obtain a Substantially Pure Mesitylene product, an additional column is used to resolve the pseudocumene and mesitylene. In one approach, for example, a column is included which is used to take an overhead pseudocumene composition as 98 wt %. However, it will be found that in most instances the TMB-rich product is sufficient and has excellent utility as a fuel or fuel blending component, without requiring the additional steps required to obtain a Substantially Pure Mesitylene product.

Auxiliary equipment, such as pumps and heat exchangers, are not shown in FIGS. 3A, 3B and 4, although additional details of such components are shown in FIGS. 5A-17A. Such auxiliary equipment is well-known and the uses and locations of this equipment in this process system will be recognized easily by those having ordinary skill in the art.

A further advantage of the described processes is that they are readily adapted to existing refinery operations. Special feed preparation is not necessary, although a targeted cut output from the catalytic reformer allows refiners optionality for more efficient conversions. Process configurations, as implemented, can be tailored to provide a wide range of valuable aromatic byproducts for gasoline and petrochemical feedstocks. An aromatic rich feed is preheated and mixed with a high-pressure feed. This is sent into the reactor segment where conversion of C2+ alkyl aromatics occurs through a non-equilibrium decoupling reaction. The decoupled effluent is then re-synthesized into a preferred slate of components that can be distilled as mesitylene and/or used as gasoline blendstocks to upgrade the overall octane of the gasoline pool. High value byproducts may include xylenes (absent ethyl-aromatics), toluene, a C9 aromatic mixture, and other gasoline and petrochemical feedstocks. Optionally, the undistilled effluent can be made free of long-chain (C8 and higher) paraffins.

Tailoring the process configurations optimizes yields and maximizes the value of various byproducts for each refinery configuration. For example, a mesitylene high-yield case for the present invention can take a C9+ reformate (methylbenzene ratio=2.1:1) and convert it into 43% mesitylene, 34% toluene, 12% C9+ aromatics, and C2 and gases. By changing the process parameters, the same C9+ reformate can yield 18% mesitylene, 64% xylenes/toluenes, 9% pseudocumene, and C2 and gases.

A refiner may instead proceed with only the HDA portion of the described reaction process, followed by alternative processing of the HDA effluent. For example, the presence of long-chain (C8 and higher) paraffin compounds blended into the gasoline pool can reduce its octane level and result in lower fuel efficiency in performance spar ignited combustion engines. In one approach, therefore, the HDA effluent is treated, such as by a less severe HDA reaction, to perform cracking of the C8 and higher paraffins. The result is an aromatic stream with significantly enhanced octane rating.

Further embodiments and aspects of the process of the present invention may be found in the following examples. These embodiments and examples are presented for purposes of illustration only and are not intended to limit the scope of the invention.

Example 1

$C_9$ Aromatic Stream

A $C_9$ aromatic stream from a naphtha reformer and related process units contains a mixture of aromatic isomers some of which have much higher octane ratings than other isomers in that stream. A typical $C_9$ stream also includes other components, as shown for example in FIG. 19. The $C_9$ stream from the naphtha reformer, or other source, may also comprise significant amounts of $C_8$ and $C_{10}$ aromatics.

Example 2

MON Improvement

By way of example, a $C_9$ aromatic stream was determined to have the chemical composition shown in FIG. 20. After the hydrodealkylation, transalkylation and isomerization, and cracking of paraffins, the resulting mixture of tri-methyl $C_9$-aromatics showed a ratio as described in FIG. 21. The resulting comparison of motor octane numbers (ASTM D2700) reveals that the original octane number of the combined $C_9$ stream was 100.7 MON, which was increased to 111 as a result of the invention. The high-value aromatic components once distilled can be blended, whereby the trimethylbenzene can be utilized directly as a high-octane aviation fuel or as a fuel component. The $C_8$ xylenes byproducts can either be processed into a BTX unit, used in high-octane gasoline blendstocks, distilled for commercial use, or they may be processed along with $C_{10}$'s via the trans-alkylation technique to make additional $C_9$ aromatics, subject to the economic tradeoffs of the process.

Example 3

Breakdown of Ethyl and Propyl Compounds

An aromatic stream comprising C8 and C9 aromatics was analyzed for chemical composition following hydrodealkylation. It was confirmed that the ethyl compounds converted to toluene and ethane, and the propyl compounds to benzene and propane, as shown in FIG. 22.

After the isomerization, dealkylation, and cracking of paraffins, the resulting components of the tri-methyl $C_9$ aromatics are more easily distilled in the absence of ethyl, propyl and butyl groups. The initial ratios are further enhanced by $C_9$'s produced during the transalkylation process as shown in FIG. 23.

The resulting comparison of motor octane numbers (ASTM D2700) showed that the original octane number of the combined $C_8$ and $C_9$ stream was 102.1 MON, which increased to 111 as a result of the invention.

Example 4

Conversion of Reformer Stream

The present invention is useful with a variety of $C_9$ aromatic streams, including those coming directly from a reformer. By way of example, a $C_9$ stream from catalytic reforming was analyzed for chemical composition and was found to contain the components as set forth in Table 3.

TABLE 3

| | Reformate Sample ($C_8$, $C_9$ & $C_{10}$ Aromatic Stream) |
|---|---|---|
| 95-63-6 | 1,2,4-trimethyl-benzene | 38.174% |
| 611-14-3 | 1-ethyl-2-methyl-benzene | 17.316% |
| 622-96-8 | 1-ethyl-4-methyl-benzene | 8.537% |
| 526-73-8 | 1,2,3-trimethyl-benzene | 7.280% |
| 108-67-8 | 1,3,5-trimethyl-benzene | 5.520% |
| 108-38-3 | 1,3-dimethyl-benzene | 3.097% |
| 141-93-5 | 1,3-diethyl-benzene | 2.779% |
| 873-49-4 | cyclopropyl-benzene | 2.088% |
| 2870-04-4 | 2-ethyl-1,3-dimethyl-benzene | 2.036% |
| 1074-43-7 | 1-methyl-3-propyl-benzene | 1.561% |
| 933-98-2 | 1-ethyl-2,3-dimethyl-benzene | 1.230% |
| 95-93-2 | 1,2,4,5-tetramethyl-benzene | 1.050% |
| 874-41-9 | 1-ethyl-2,4-dimethyl-benzene | 1.011% |
| 103-65-1 | propyl-benzene | 0.915% |
| 95-93-2 | 1,2,4,5-tetramethyl-benzene | 0.715% |
| 535-77-3 | m-Cymene | 0.697% |
| 135-98-8 | S-Butyl-benzene | 0.657% |
| 488-23-3 | 1,2,3,4-tetramethyl-benzene | 0.479% |
| 934-80-5 | 4-ethyl-1,2-dimethyl-benzene | 0.396% |
| 106-42-3 | P-Xylene | 0.319% |
| 91-20-3 | Napthalene | 0.267% |
| 135-98-8 | S-Butyl-benzene | 0.250% |
| 104-51-8 | butyl-benzene | 0.224% |
| 2870-04-4 | 2-ethyl-1,3-dimethyl-benzene | 0.201% |
| 135-01-3 | 1,2-diethyl-benzene | 0.162% |
| 768-49-0 | (2-methyl-1-propenyl)-benzene | 0.149% |
|  | Unknown | 2.890% |
|  |  | 100.000% |

After processing in accordance with the present invention, including hydrodealkylation and transalkylation/isomerization, the resulting mixture of tri-methyl $C_9$-aromatics produces products as shown in Table 4.

Table 4 further highlights specifically how this invention separates the various compounds via hydrodealkylation of the ethyl and propyl groups resulting in ethane, propane, benzene, toluene and xylene, and isomerization of the methyl benzenes, yielding the trimethyl benzenes. Referring to FIG. 19, it is shown, for example, that 1-ethyl-2-methyl-benzene yields ethane and toluene, and 1,3-diethyl-benzene is broken down to ethane and benzene.

TABLE 4

| Reformate Sample (C8, C9 & C10 Aromatic Stream) | DEALKYLATION SYNTHESIS-FOR DISTILLATION | | | | | | |
|---|---|---|---|---|---|---|---|
| | $C_2H_6$ Ethane | Propane | $n$-$C_4H_{10}$ Butane | Isobutane | $C_6H_6$ Benzene | Toluene | $C_8H_{10}$ Xylene |
| 1,2,4-trimethyl-benzene | | | | | | | |
| 1-ethyl-2-methyl-benzene | X | | | | | X | |
| 1-ethyl-4-methyl-benzene | X | | | | | X | |
| 1,2,3-trimethyl-benzene | | | | | | | |
| 1,3,5-trimethyl-benzene | | | | | | | |
| 1,3-dimethyl-benzene | | | | | | | X |
| 1,3-diethyl-benzene | X | | | | X | | |
| cyclopropyl-benzene | | X | | | X | | |
| 2-ethyl-1,3-dimethyl-benzene | X | | | | | | X |
| 1-methyl-3-propyl-benzene | | X | | | | X | |
| 1-ethyl-2,3-dimethyl-benzene | | | | | | X | X |
| 1,2,4,5-tetramethyl-benzene | | | | | | | |
| 1-ethyl-2,4-dimethyl-benzene | X | | | | | | X |
| propyl-benzene | | X | | | X | | |
| 1,2,4,5-tetramethyl-benzene | | | | | | | |
| m-Cymene | | | | | | | |
| S-Butyl-benzene | | | | X | X | | |
| 1,2,3,4-tetramethyl-benzene | | | | | | | |
| 4-ethyl-1,2-dimethyl-benzene | X | | | | | | X |
| P-Xylene | | | | | | | X |
| Napthalene | | | | | | | |
| S-Butyl-benzene | | | | X | X | | |
| butyl-benzene | | | X | | X | | |
| 2-ethyl-1,3-dimethyl-benzene | X | | | | | | X |
| 1,2-diethyl-benzene | X | | | | X | | |
| (2-methyl-1-propenyl)-benzene | | X | | | | X | |
| Unknown | | | | | | | |
| | −89° C. | | −1° C. | | 80° C. | | 135° C. |

Following processing in accordance with the present invention, an initial feed is converted as shown in Table 5 (based on vol %).

TABLE 5

| | Prior to Processing | After Processing |
|---|---|---|
| Mesitylene | 7.37% | 24.61% |
| Pseudocumene | 37.52% | 11.94% |
| Mixed C9's/C10's+ | 50.60% | 9.62% |
| Mixed-Xylenes | 4.51% | 38.71% |
| Toluene | 0 | 6.75% |

As a result of the decoupling of the ethyl, propyl and butyls, the capability to fractionate the trimethylbenzenes is significantly simplified due to the difference in the boiling point of the 1,2,3-trimethyl benzene. See FIG. 24. This allows for a variety of blending combinations to meet various grades of high performance gasoline and aviation fuel. This is a major feature of this invention.

Example 5

Sample Heat and Material Balance

Figure 5A:
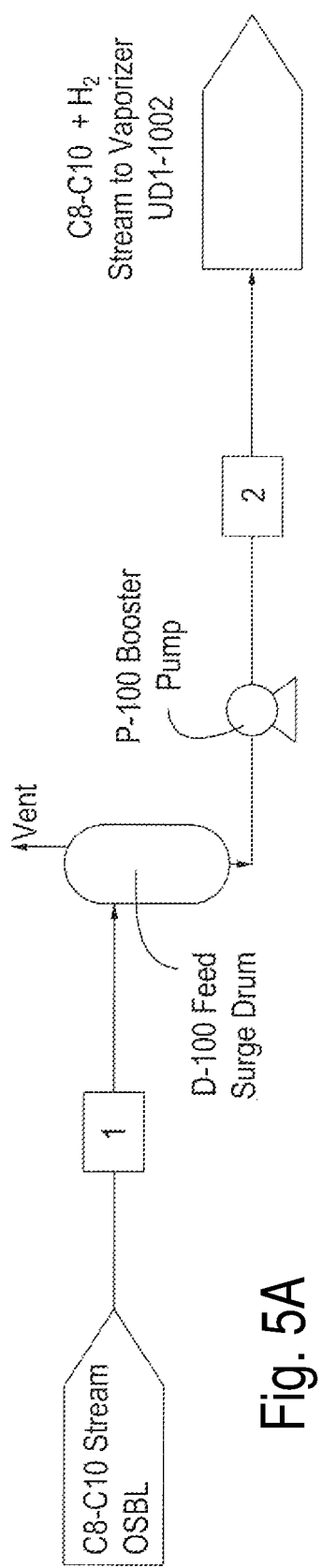
Figure 6A:
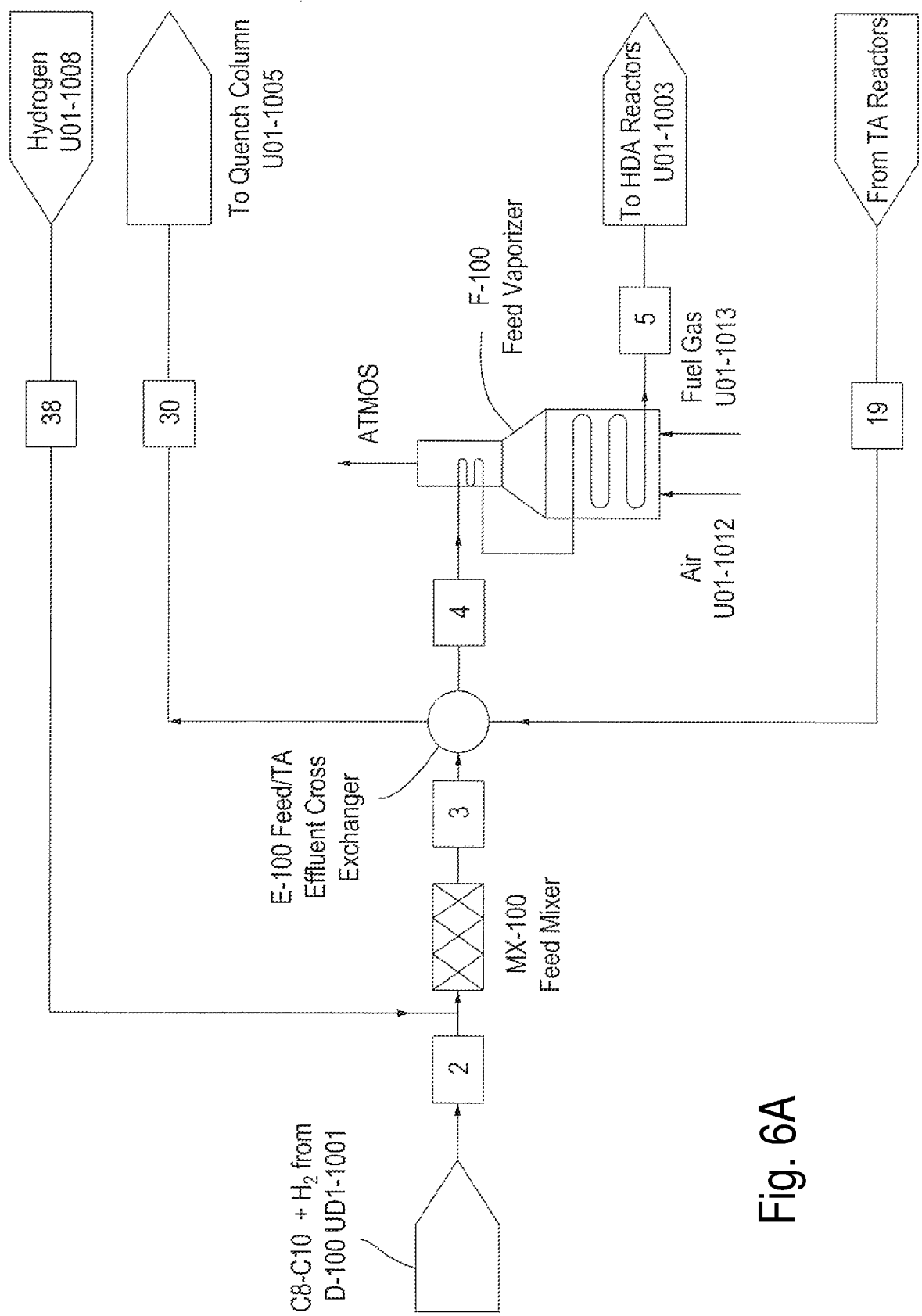
Figure 7A:
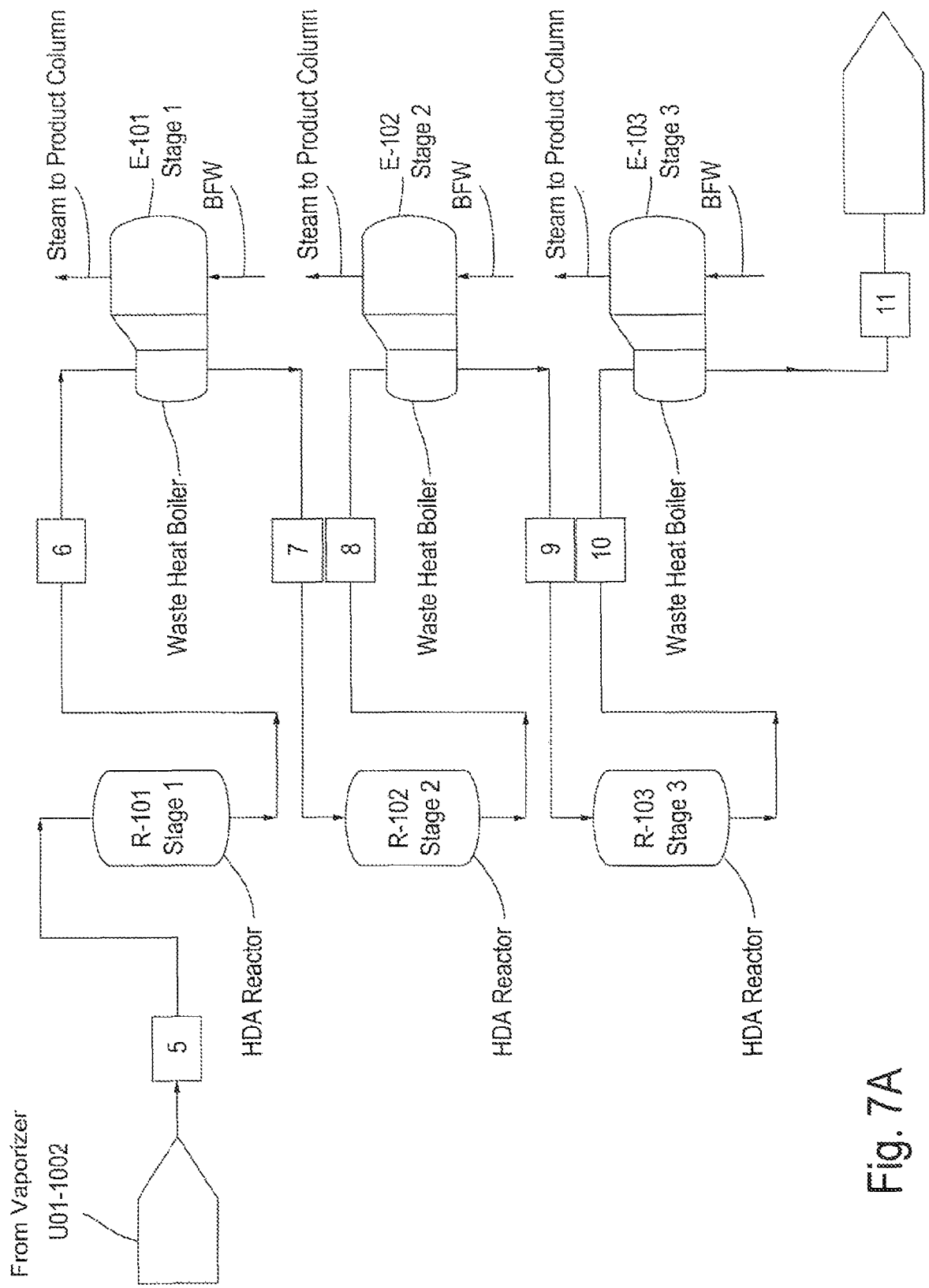
Figure 8A:
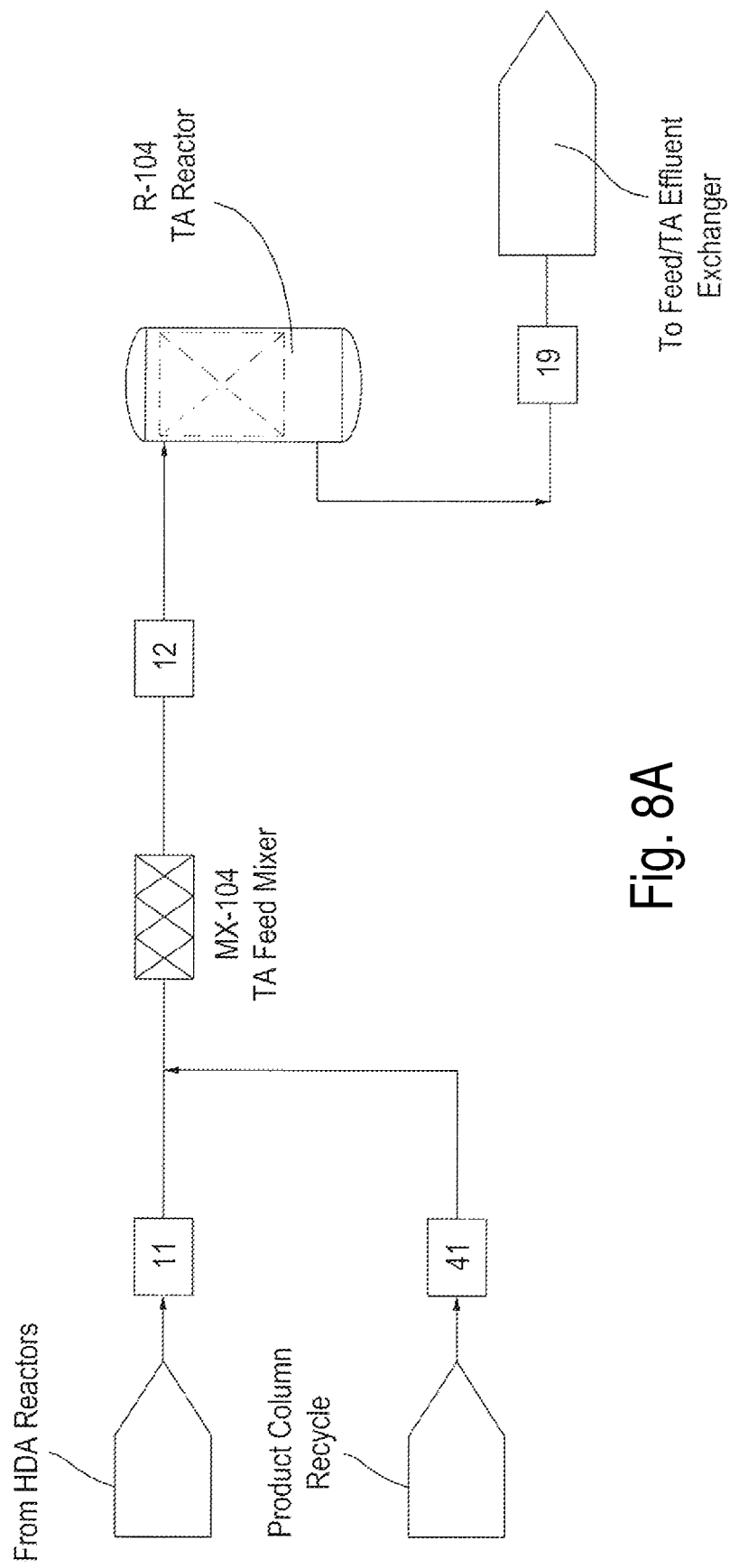
Figure 9A:
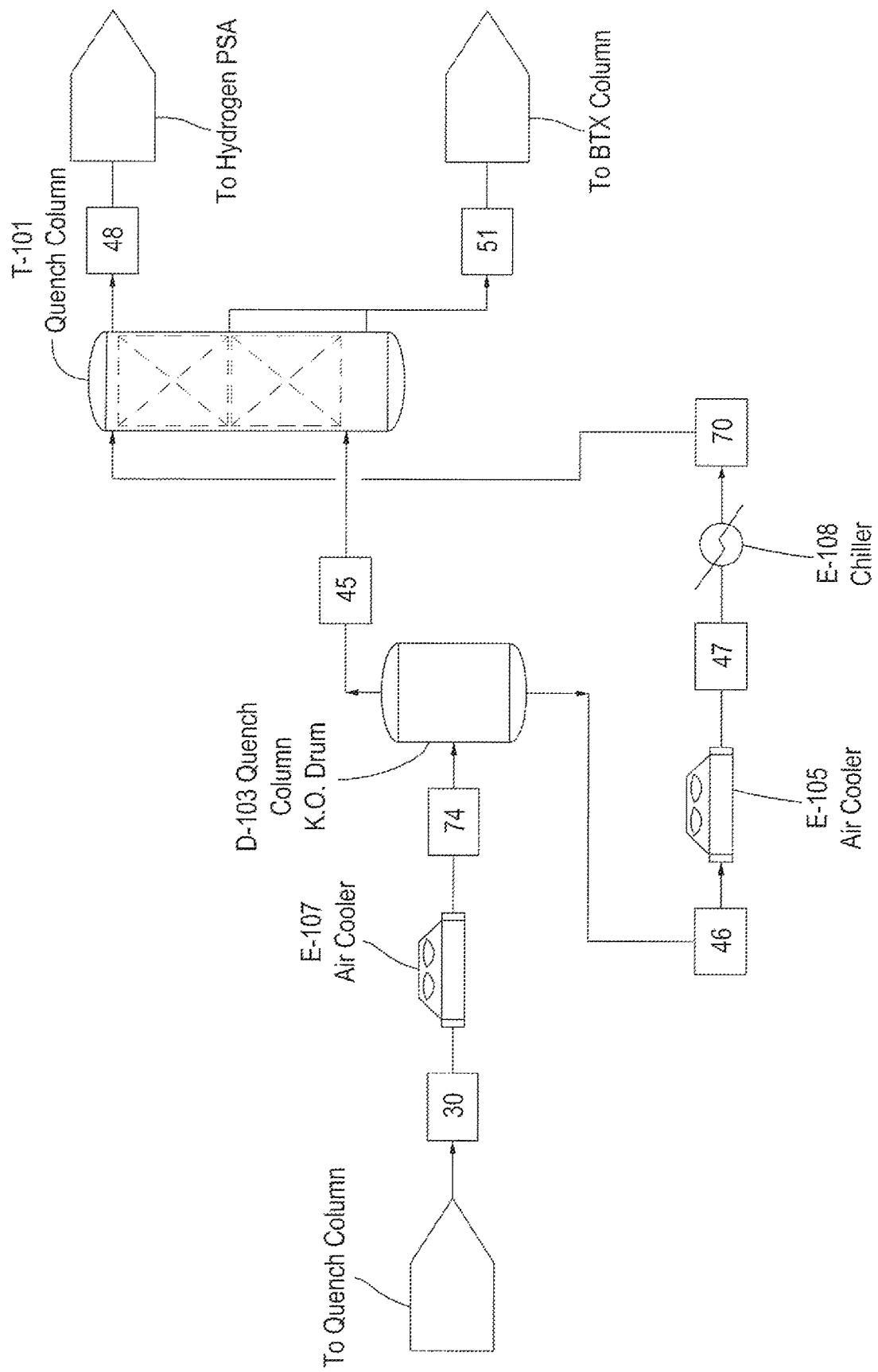
Figure 10A:
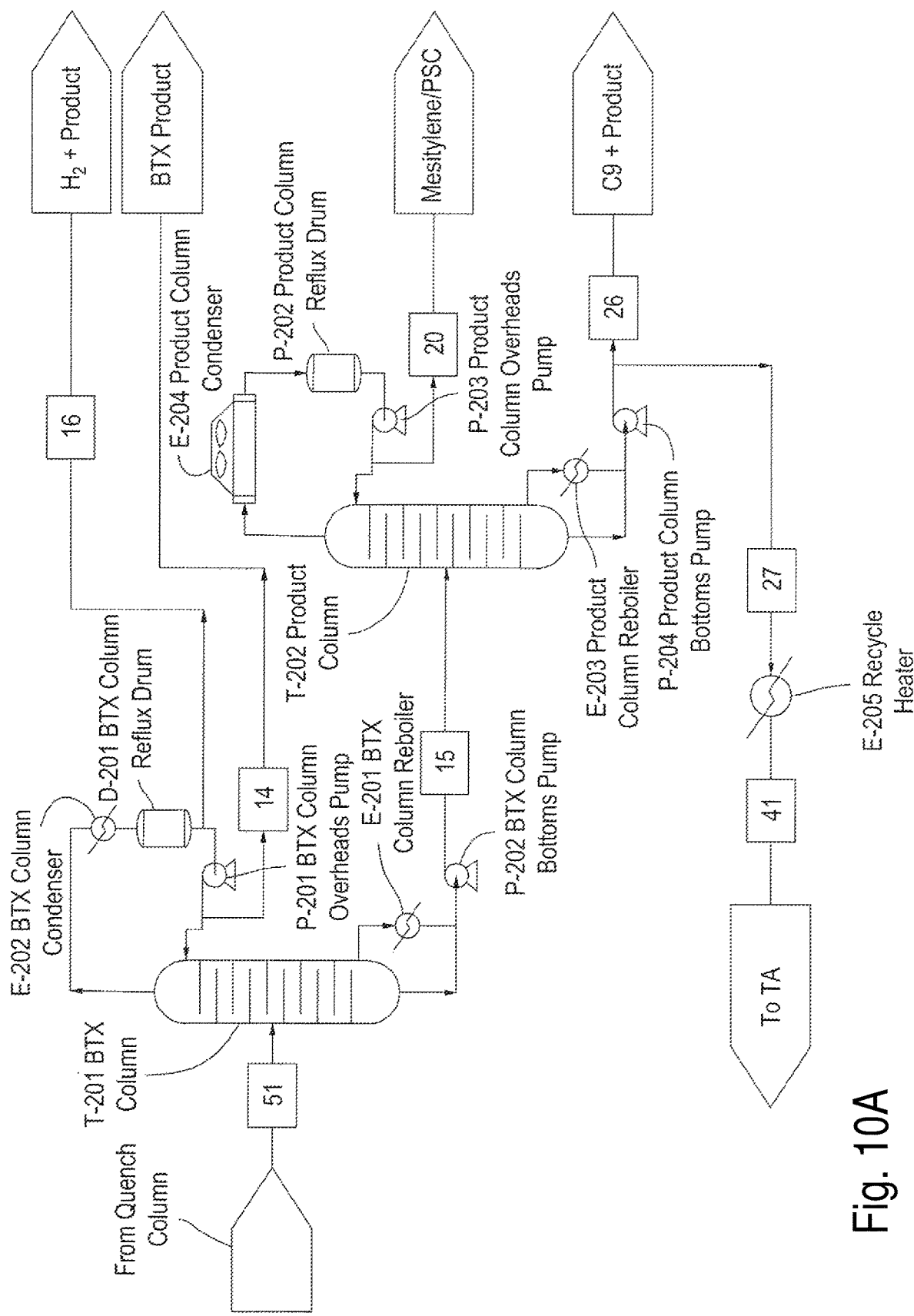
Figure 11A:
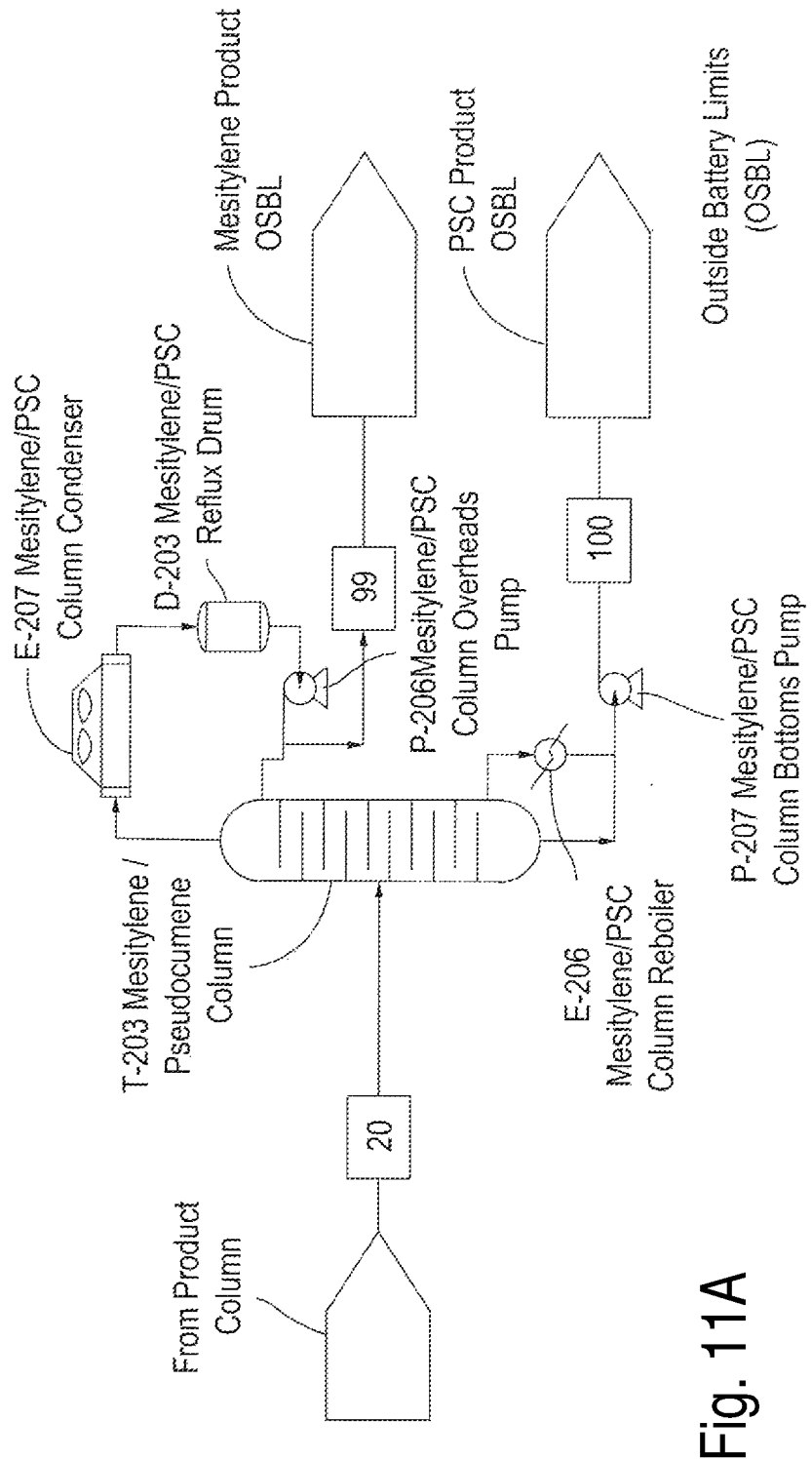
Figure 12A:
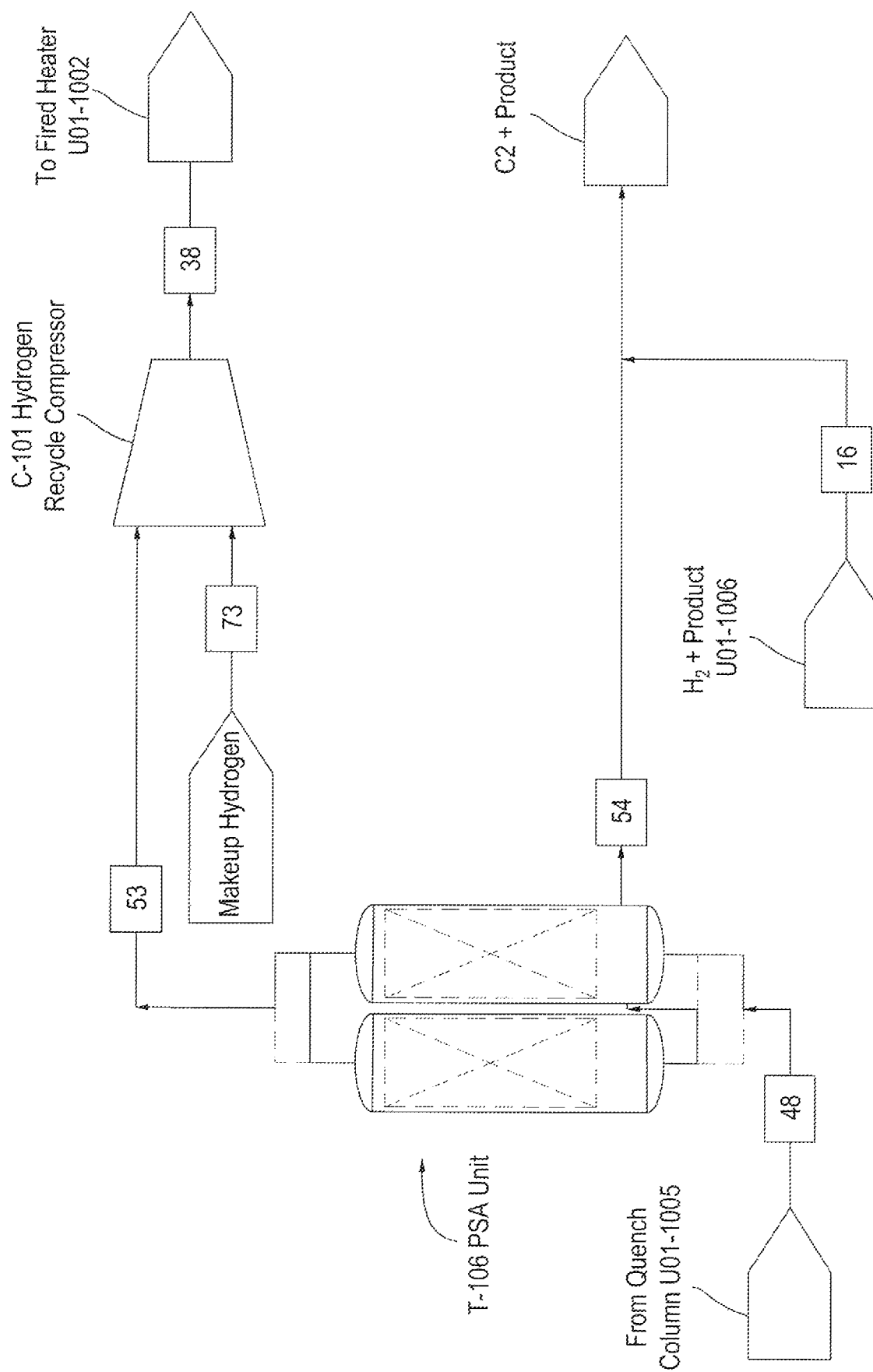
Figure 13A:
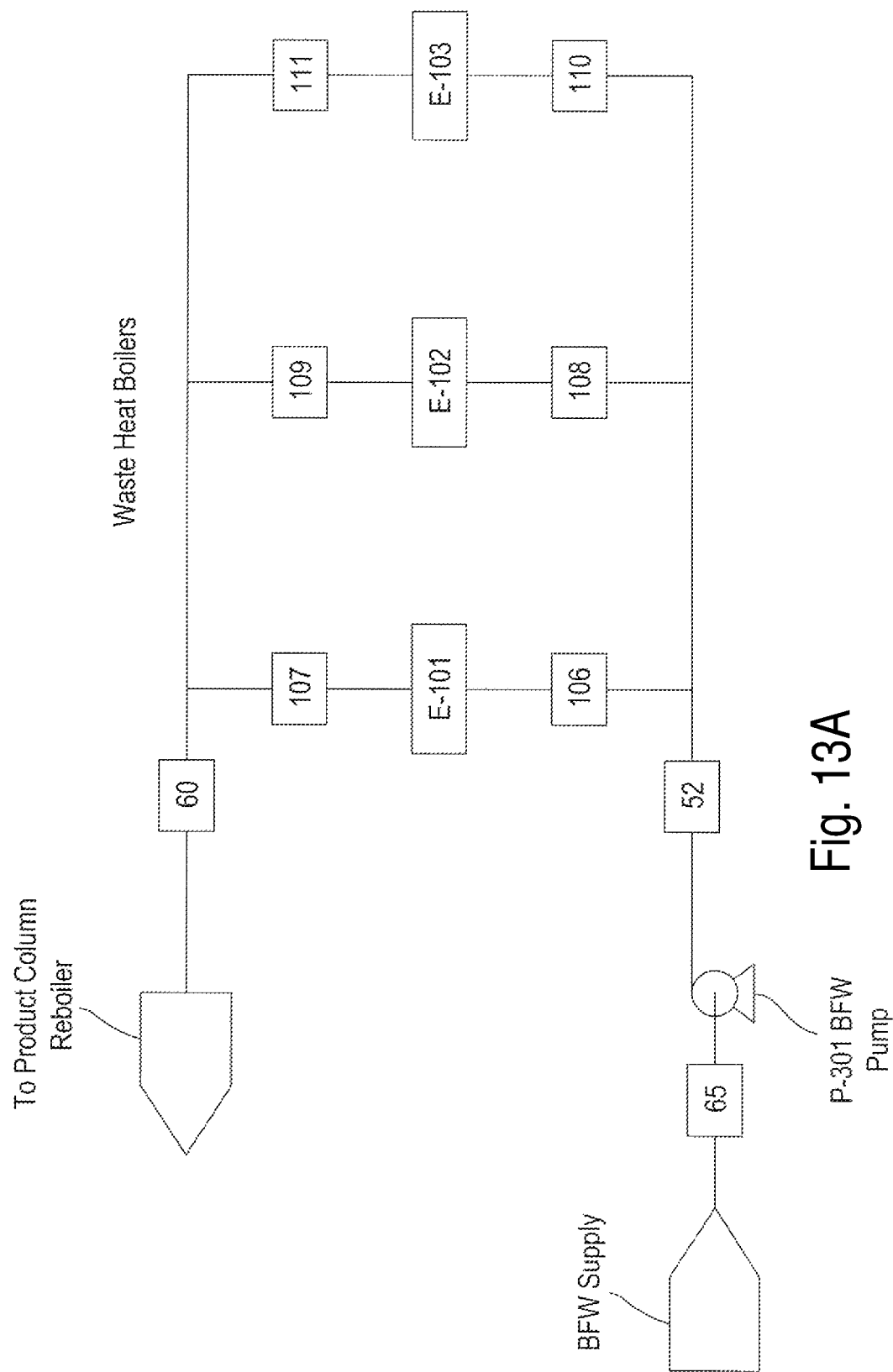
Figure 14A:
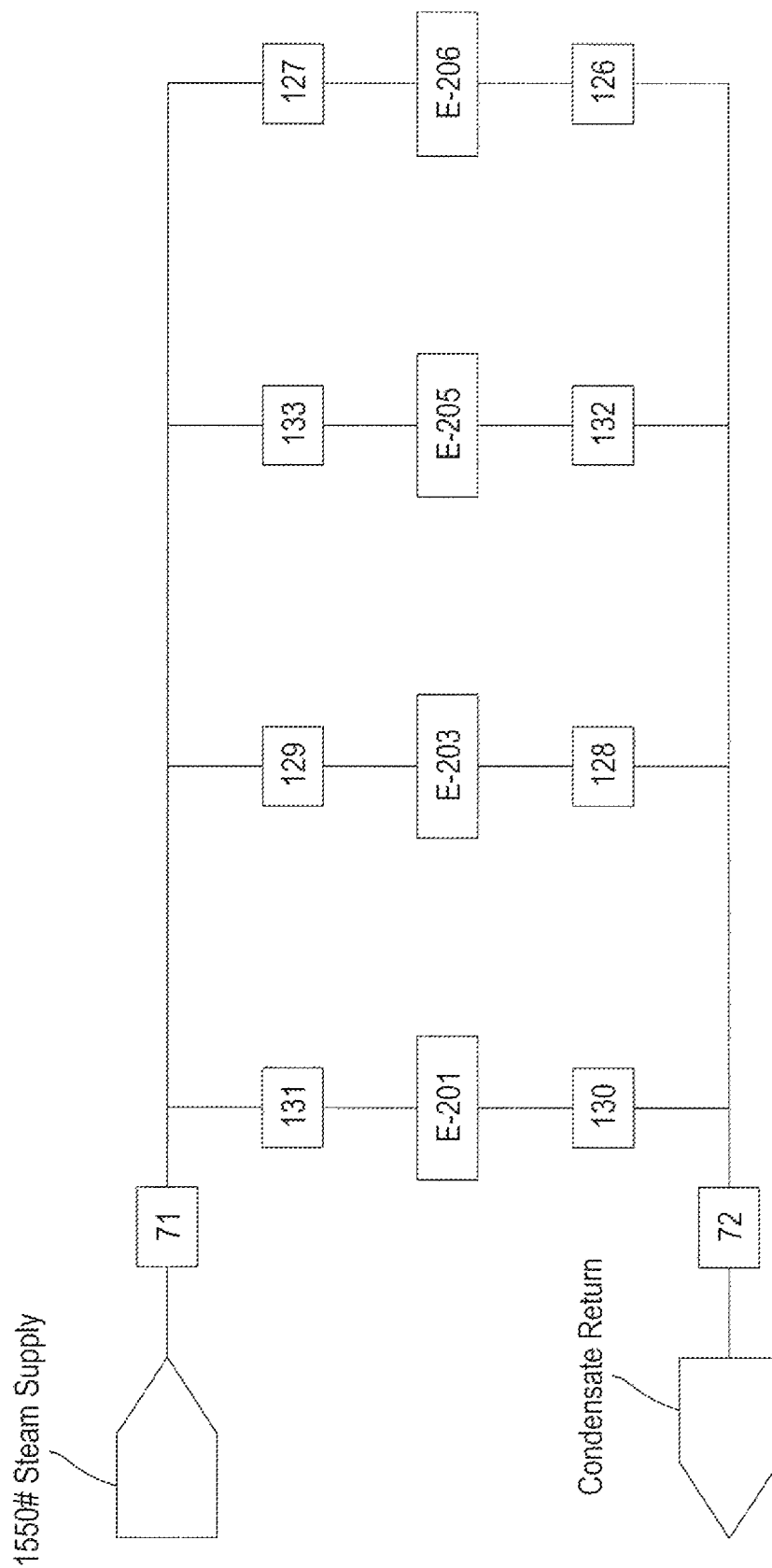
Figure 15A:
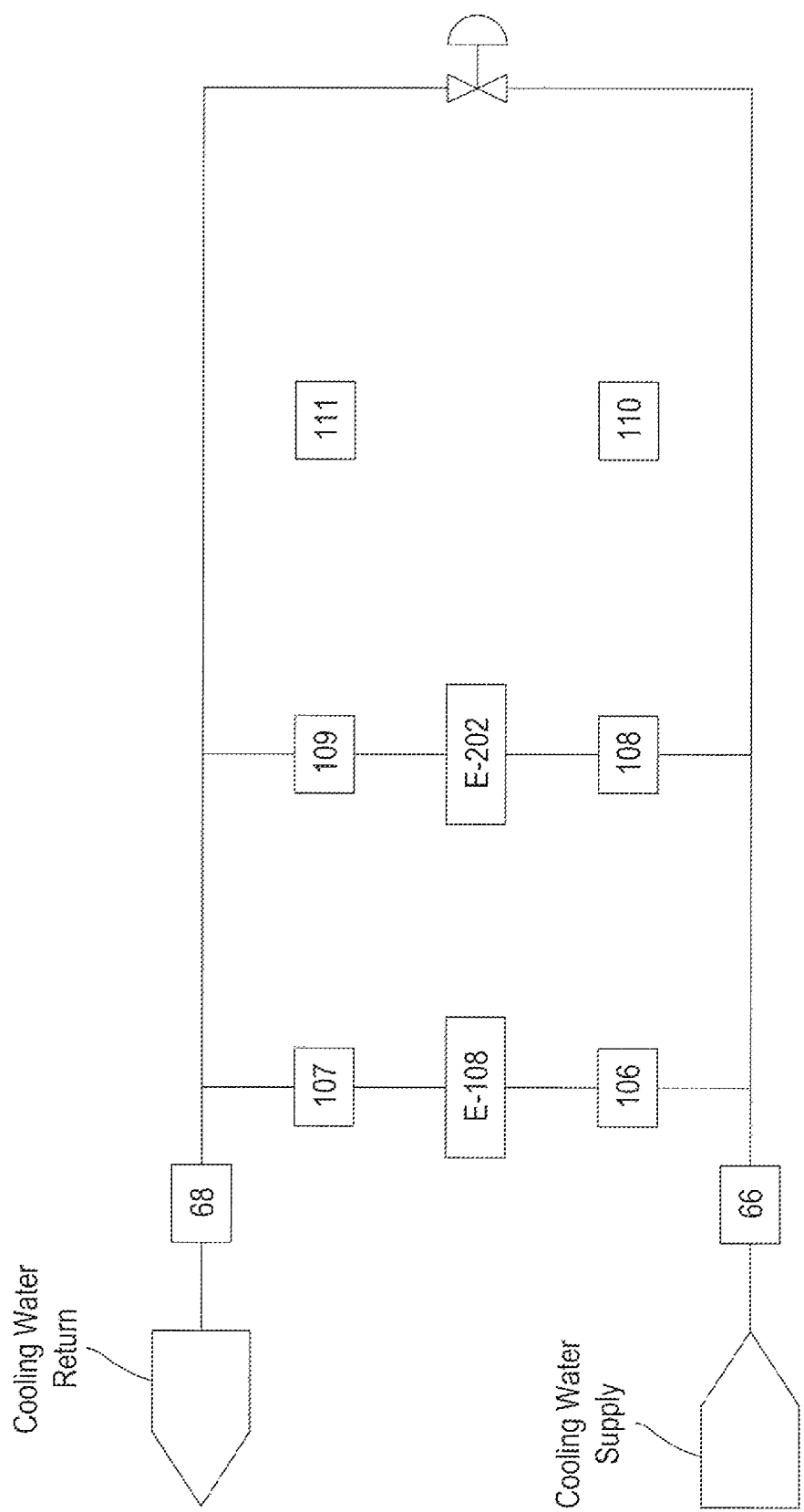
Figure 16A:
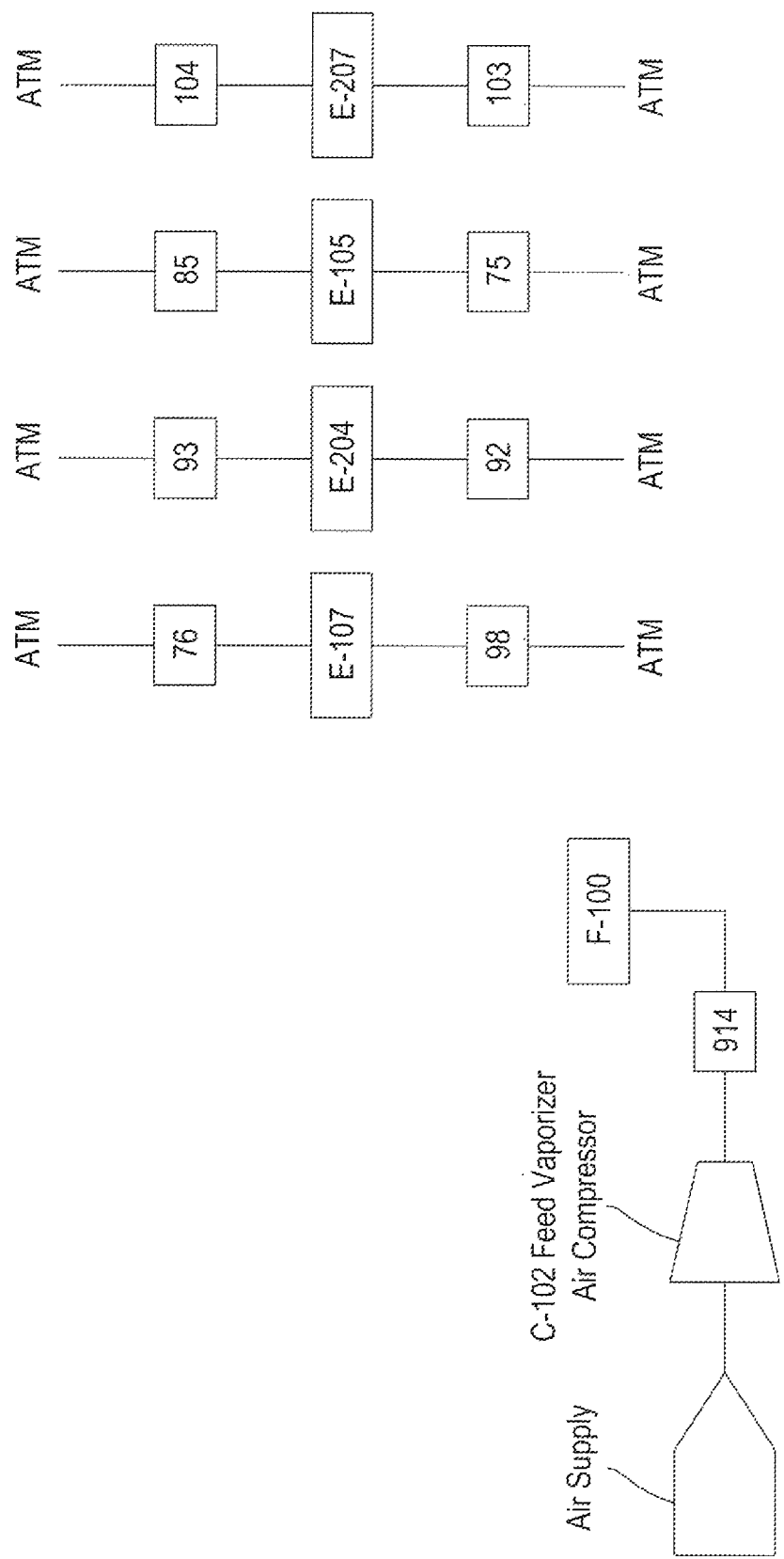
Figure 17A:
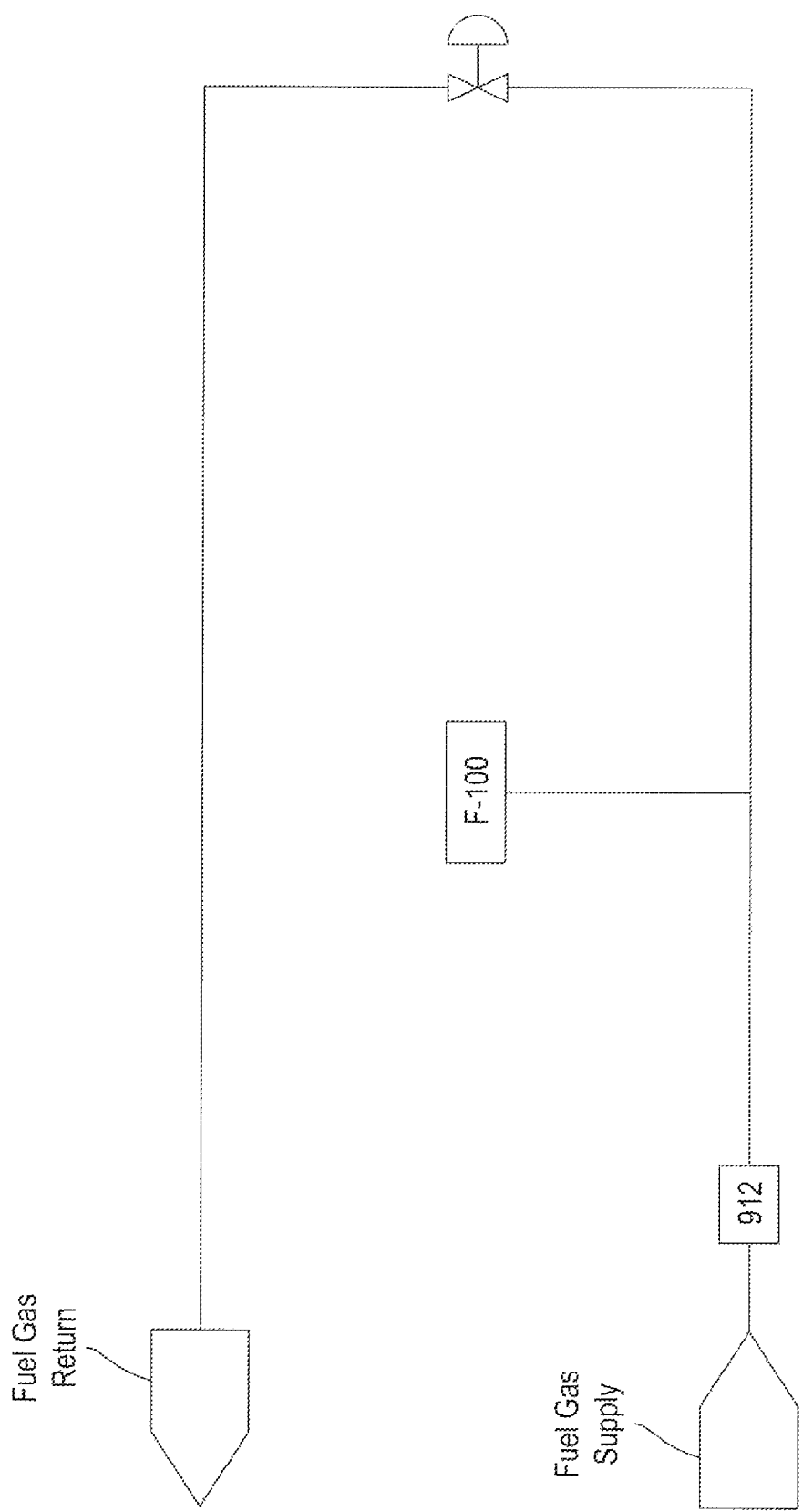

By way of further example, a heat and material balance has been prepared based on a typical C8-C10 feed stream. The entire system is shown diagrammatically in FIGS. 5A-17A. Referring to FIG. 5A, for example, there is shown the initial feed and preliminary processing thereof for passing the feed to the system. The compositions of the feed and of other system streams are presented in FIGS. 5B-17B, corresponding to the process streams shown in FIGS. 5A-17A, respectively.

While the invention has been illustrated and described in detail in the drawings and foregoing description, the same is to be considered as illustrative and not restrictive in character, it being understood that only exemplary embodiments have been shown and described. All changes, equivalents, and modifications that come within the spirit of the inventions defined by the following claims are desired to be protected. All publications, patents, and patent applications cited in this specification are herein incorporated by reference as if each individual publication, patent, or patent application was specifically and individually indicated to be incorporated by reference and set forth in its entirety herein.

The invention claimed is:

1. A method for the production of a C9 aromatic product with increased-octane number from an aromatic composition comprising aromatic components including methyl benzenes and $C_2$ and/or higher alkyl benzenes, comprising:
   a. hydrodealkylating the aromatic components to convert the $C_2$ and/or higher alkyl benzenes to the corresponding alkanes and dealkylated aromatics including benzene and toluene, while retaining the methyl benzenes;

b. after step a and before step c., removing the benzene and toluene from the methyl benzenes using a first aromatic lights column;

c. transalkylating the methyl benzenes to redistribute the methyl groups among the methyl benzenes to form trimethylbenzenes and other methylated benzenes;

d. after step c. and before step e., passing the trimethylbenzenes through a second aromatic lights column to remove C6-C8 aromatics;

e. isomerizing the trimethylbenzenes to produce an isomerized product; and f. recovering an increased-octane number product from the isomerized product.

2. The method of claim 1 in which said hydrodealkylating is performed above 350° C.

3. The method of claim 1 in which said transalkylating is performed at less than 275° C.

4. The method of claim 3 in which said hydrodealkylating is performed above 350° C.

5. The method of claim 4 which further includes combining elemental hydrogen with the aromatic components for hydrodealkylating.

6. The method of claim 5 which includes recovering C10 and higher aromatics and recycling them to said hydrodealkylating.

7. The method of claim 6 in which said recovering C10 and higher aromatics comprises recovering them from the isomerized product.

8. The method of claim 1 which further includes, after step a, combining supplemental methylated aromatics with the methyl benzenes, prior to step b. and after step c.

9. The method of claim 8 which includes recovering C10 and higher aromatics and recycling them to said transalkylating.

10. The method of claim 9 in which said recovering C10 and higher aromatics comprises recovering them from the isomerized product.

11. The method of claim 1 in which said hydrodealkylating and said transalkylating are performed together.

12. The method of claim 1 in which said recovering an increased-octane product is by distillation.

13. The method of claim 1 in which the aromatic components comprise ethyl toluenes and in which said hydrodealkylating removes at least 75 vol % of the ethyl toluenes.

14. The method of claim 13 in which said hydrodealkylating removes at least 90 vol % of the ethyl toluenes.

15. The method of claim 1 in which the aromatic components further comprise C8 and higher paraffins and wherein said hydrodealkylating includes catalytic cracking of C8 and higher paraffins.

16. The method of claim 15 in which said hydrodealkylating and said transalkylating are performed separately and at different temperatures.

17. The method of claim 16 in which the increased-octane number product further comprises mesitylene, and further comprising treating the increased-octane number product to prepare a substantially pure mesitylene product.

18. The method of claim 15 in which said hydrodealkylating is performed above 350° C.

19. The method of claim 15 in which said transalkylating is performed at less than 275° C.

20. The method of claim 19 in which said hydrodealkylating is performed above 350° C.

21. The method of claim 10 in which said hydrodealkylating is performed in the presence of a hydrodealkylating catalyst, and the transalkylating is performed in the presence of a transalkylating catalyst.

22. The method of claim 15 which further includes, following said hydrodealkylating, removing paraffins from the effluent of step a.

23. The method of claim 22 in which said removing paraffins comprises removing gaseous paraffins.

24. The method of claim 23 in which said removing gaseous paraffins comprises passing the effluent of step a. through a quench column and removing hydrogen and light alkanes.

25. The method of claim 24 which further includes recycling hydrogen removed in the quench column for use in said hydrodealkylating.

26. The method of claim 1 which further includes recycling benzene and/or toluene removed in the first aromatic lights column for use in said hydrodealkylating.

* * * * *